(12) United States Patent
Nakasuji et al.

(10) Patent No.: US 7,312,449 B2
(45) Date of Patent: Dec. 25, 2007

(54) ELECTRON BEAM SYSTEM AND METHOD OF MANUFACTURING DEVICES USING THE SYSTEM

(75) Inventors: Mamoru Nakasuji, Kanagawa (JP); Takao Kato, Tokyo (JP); Tohru Satake, Kanagawa (JP); Kenji Watanabe, Kanagawa (JP); Takeshi Murakami, Tokyo (JP); Nobuharu Noji, Kanagawa (JP)

(73) Assignee: Ebara Corporation, Tokyo (JP)

( * ) Notice: Subject to any disclaimer, the term of this patent is extended or adjusted under 35 U.S.C. 154(b) by 25 days.

(21) Appl. No.: 11/034,873

(22) Filed: Jan. 14, 2005

(65) Prior Publication Data

US 2005/0133733 A1    Jun. 23, 2005

Related U.S. Application Data

(62) Division of application No. 10/337,420, filed on Jan. 7, 2003, now Pat. No. 6,853,143.

(30) Foreign Application Priority Data

| Jan. 9, 2002 | (JP) | 2002/2233 |
| Jan. 10, 2002 | (JP) | 2002/3317 |
| Jan. 16, 2002 | (JP) | 2002/6971 |

(51) Int. Cl.
  *G01N 23/00*  (2006.01)
(52) U.S. Cl. .................. 250/311; 250/310; 250/492.2
(58) Field of Classification Search ............... 250/311
  See application file for complete search history.

(56) References Cited

U.S. PATENT DOCUMENTS 5,359,197 A    10/1994    Komatsu et al.

5,892,224 A    4/1999    Nakasuji
5,973,332 A  *  10/1999    Muraki et al. ........... 250/492.2

(Continued)

FOREIGN PATENT DOCUMENTS

EP    0 366 005    5/1990

(Continued)

OTHER PUBLICATIONS

B.J. Thompson et al., "Fluctuations in Space-Charge-Limited Currents at Moderately High Frequencies" RCA Review 4 (1940), pp. 441-472.

*Primary Examiner*—Jack I. Berman
*Assistant Examiner*—Phillip Johnston
(74) *Attorney, Agent, or Firm*—Westerman, Hattori, Daniels & Adrian, LLP.

(57) ABSTRACT

An electron beam system wherein a shot noise of an electron beam can be reduced and a beam current can be made higher, and further a shaped beam is formed by a two-stage lenses so as to allow for an operation with high stability. In this electron beam system, an electron beam emitted from an electron gun is irradiated onto a sample and secondary electrons emanated from the sample are detected. The electron gun is a thermionic emission type and designed to operate in a space charge limited condition. A shaping aperture and a NA aperture are arranged in front locations of the electron gun. An image of the shaping aperture formed by an electron beam emitted from the thermionic emission electron gun is focused onto a surface of the sample through the two-stage lenses.

9 Claims, 14 Drawing Sheets

U.S. PATENT DOCUMENTS

| | | |
|---|---|---|
| 6,087,667 A | 7/2000 | Nakasuji et al. |
| 6,310,341 B1 | 10/2001 | Todokoro et al. |
| 6,365,897 B1 | 4/2002 | Hamashima et al. |
| 6,476,390 B1 * | 11/2002 | Murakoshi et al. ......... 250/310 |
| 6,555,816 B1 | 4/2003 | Sawahata et al. |
| 6,583,413 B1 | 6/2003 | Shinada et al. |
| 6,593,152 B2 | 7/2003 | Nakasuji et al. |
| 2002/0088940 A1 | 7/2002 | Watanabe et al. |
| 2002/0148961 A1 | 10/2002 | Nakasuji et al. |

FOREIGN PATENT DOCUMENTS

| | | |
|---|---|---|
| JP | 2002-195964 | 7/2002 |

* cited by examiner

Fig. 10
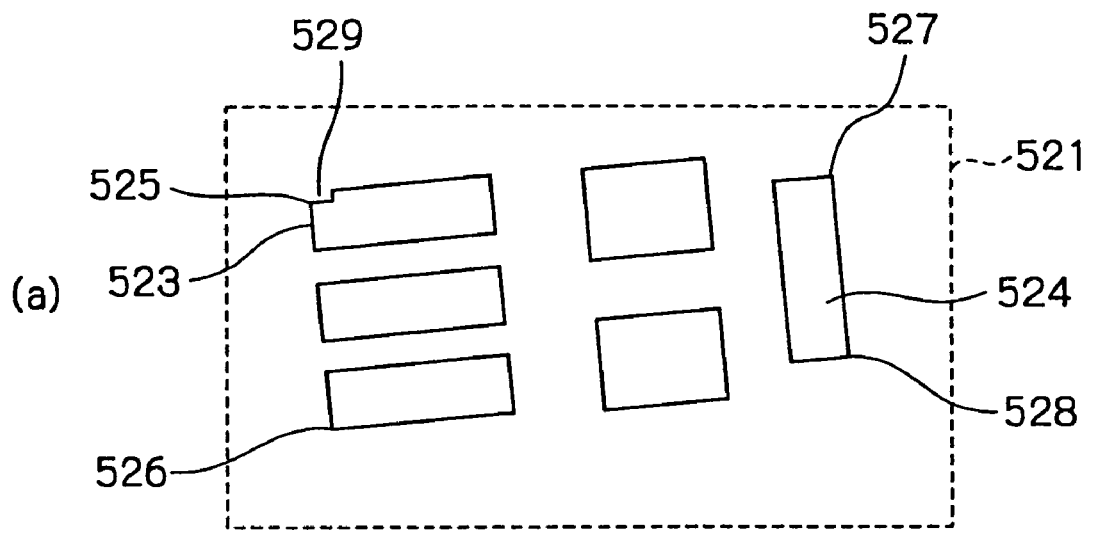
(a)
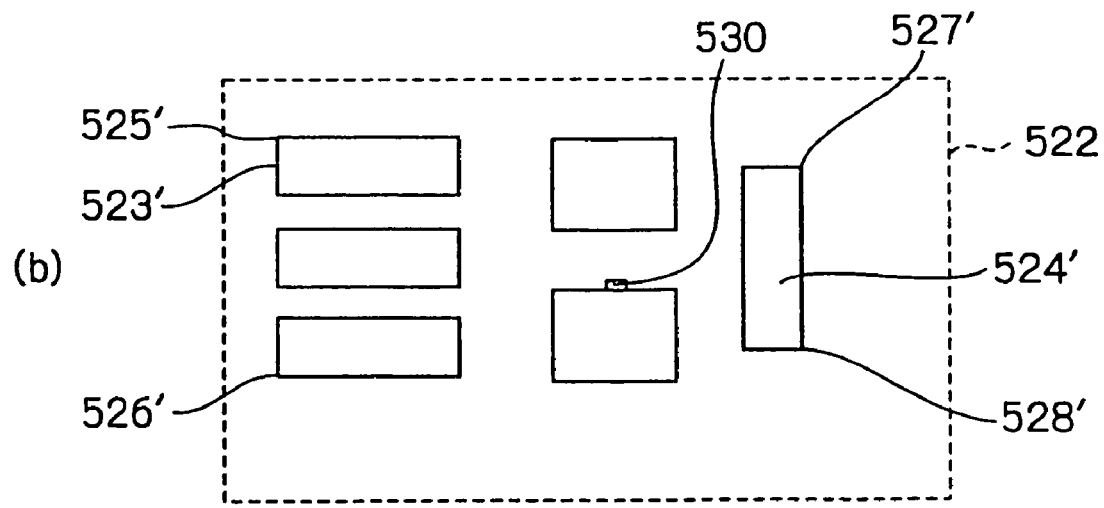
(b)
(c)

Fig. 13
(a)
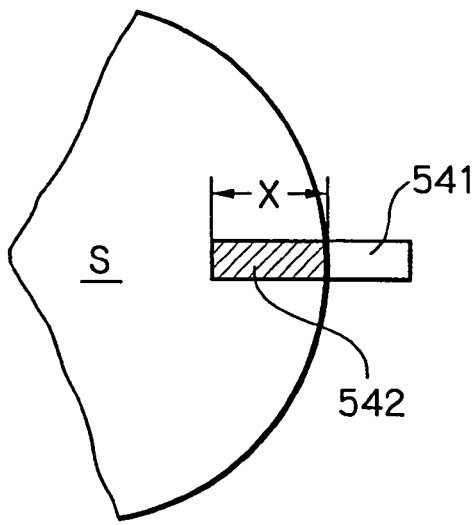
(b)
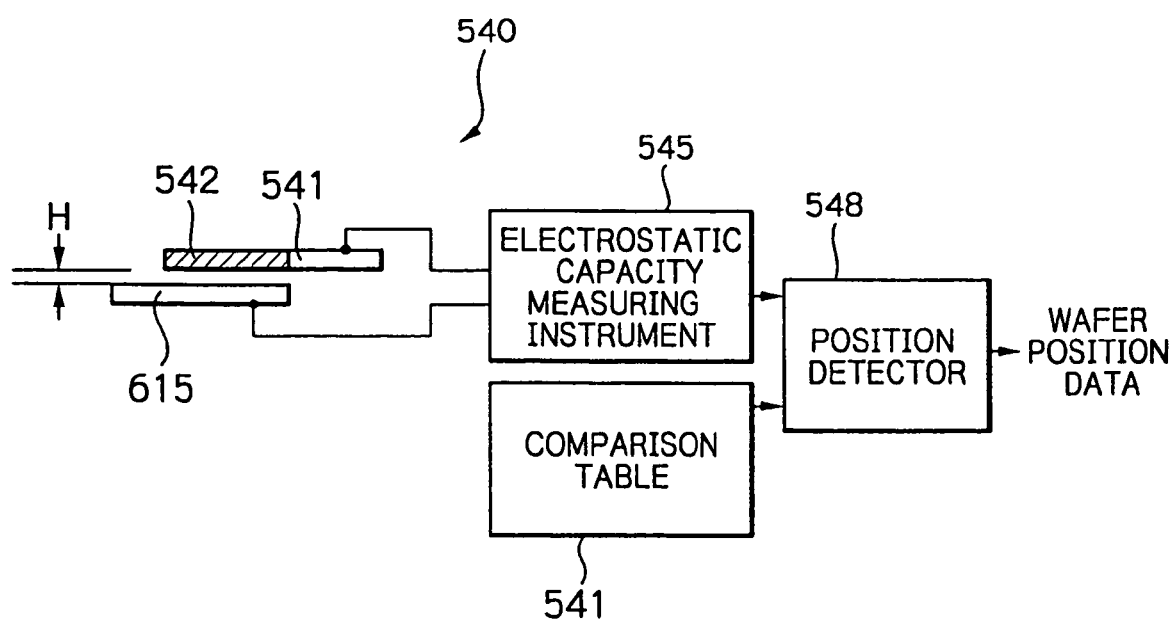

Fig. 14
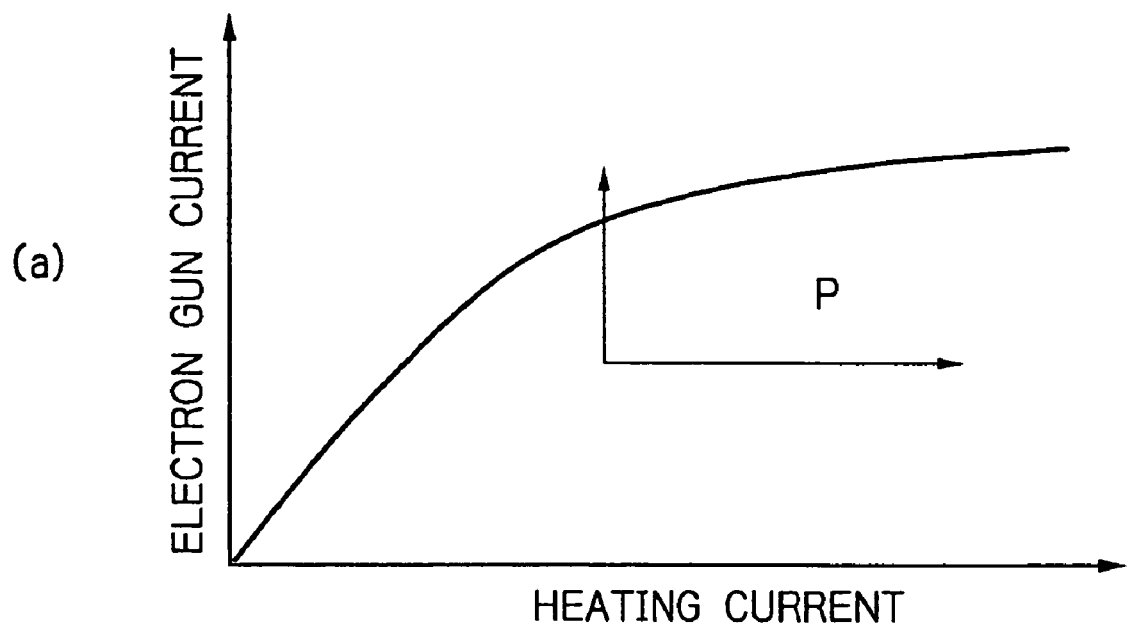
(a)
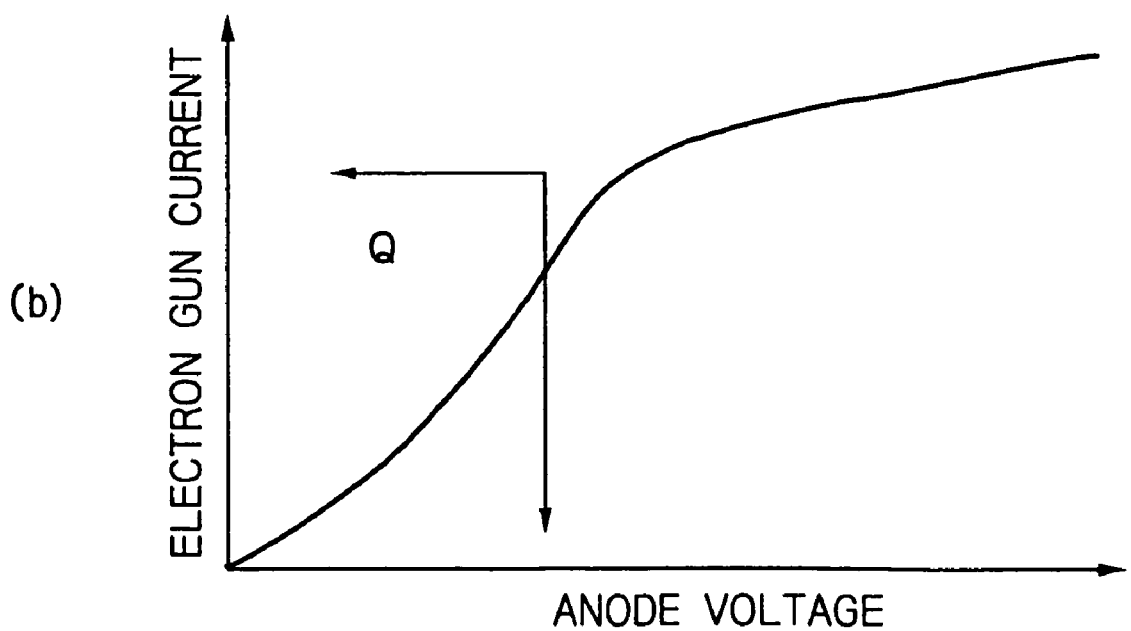
(b)

ELECTRON BEAM SYSTEM AND METHOD OF MANUFACTURING DEVICES USING THE SYSTEM

This application is a divisional of U.S. patent application Ser. No. 10/337,420 filed on Jan. 7, 2003 now U.S. Pat. No. 6,853,143, which is incorporated by reference in its entirety. Priority under 35 U.S.C. §120 is hereby claimed for benefit of the filing date of U.S. patent application Ser. No. 10/337,420.

BACKGROUND OF THE INVENTION

The present invention relates to an electron beam system, a defect inspection apparatus for a device, which employs the same electron beam system, and a manufacturing method of a device using the same defect inspection apparatus, and more specifically, relates to an electron beam system which can evaluate a sample (a semiconductor wafer) having a device pattern with a minimum line width equal to or less than 0.1 µm with both a high throughput and high reliability, a defect inspection apparatus for a device, which employs the same electron beam system, and a manufacturing method of a device which can improve a yield thereof by evaluating a wafer after it has been processed using the same defect inspection apparatus.

The present invention also relates to an electron beam system and a defect inspection method for evaluating a device, such as a wafer or a mask, having a pattern with a minimum line width in a range of 0.1 micron, and also to a method for manufacturing a device with a high yield by using the same system and a defect inspection method.

The present invention further relates to a method for simplifying a registration (positioning) of an inspection apparatus in which an electron beam is irradiated against a sample and secondary electrons emanated from the sample are detected and then processed to thereby obtain an SEM (Scanning Electron Microscope) image of a fine geometry on a surface of the sample, and thus carry out evaluation thereof. The fine geometry on the sample surface may be, for example, on a semiconductor wafer or a mask having a high-density pattern with a minimum line width equal to or less than 0.1 µm. The present invention also relates to a manufacturing method of a semiconductor device using such an inspection apparatus.

One such electron beam system has been suggested for evaluating a sample having a device pattern with a minimum line width equal to or less than 0.1 µm, in which a shaped electron beam is demagnified (contracted) to be narrower and irradiated onto a sample and then secondary electrons emanated from the sample are detected so as to evaluate the sample. In such a system, an optical system for shaping the electron beam has employed at least a three-stage of lenses. Besides, when it is intended to form such a narrow electron beam equal to or less than 0.1 µm, a demagnification crossover image type beam has been employed. Further, it is required to increase an intensity of the electron beam in order to provide evaluation with higher reliability, and in this case a thermoelectric field emission (schottky) cathode electron gun has been used so as to obtain a high current beam of 0.1 µm or smaller.

Such an electron beam system has been known, in which a primary electron beam emitted from an electron gun is demagnified to be narrower so as to irradiate a sample, such as a wafer or a mask, and a secondary electron beam, which has been emanated from the sample through this irradiation, is detected, to thereby detect any defects or to measure a line width on the sample. Further, it has been also known that an electron beam is irradiated on a sample and thereby charges are introduced to a pattern on the sample so as to induce a voltage, which is in turn measured and thus an electric parameter of the sample is measured.

In the prior art, for measuring the voltage induced in the pattern on the surface of the sample, there has been employed one such method in which a hemispherical mesh filter is provided, and the secondary electrons emanated from the sample surface are returned to the sample surface side or introduced into a detector arranged behind the mesh in dependence on a potential of the pattern from which the secondary electrons have been emanated, thus carrying out measurement of the potential of the pattern. An electron gun in an electron beam system to be used in such a method may be in most cases one designated as a schottky type by Zr-W having a magnified intensity. Further, a demagnified crossover image formed by the electron gun has been commonly used as a probe current for injecting charges into the sample to measure the voltage of the pattern.

One such inspection apparatus has been well known that uses a scanning electron microscope to inspect a subject (sample), such as a semiconductor wafer and so on. In this inspection apparatus, a narrowly demagnified electron beam is used to conduct raster scanning with a raster scanning width of an extremely narrow space, and then secondary electrons emanated from the subject are detected by a detector so as to form an SEM image, wherein two SEM images for corresponding locations in two different samples are compared to each other to detect any defects.

A lithography apparatus which comprises an electron optical system and which uses an electron beam to form a fine geometry on a surface of a sample such as a semiconductor wafer requires position alignment or a registration of high precision between the electron optical system and the sample. In order to satisfy this requirement, one method has been employed that uses the electron optical system of the lithography apparatus to detect an alignment mark on the sample to accomplish the position alignment, and also another method has been employed, in which an optical microscope is further provided in addition to the electron optical system so as to perform rough alignment (a roughly controlled position alignment) through an observation across an enlarged field of view by using the optical microscope and also fine alignment (a high magnification position alignment) by using the electron optical system of the lithography apparatus. However, such high precision alignment is not necessarily required in an inspection apparatus.

SUMMARY OF THE INVENTION

However, it is problematic that although in a schottky electron gun, a beam current three to ten times higher as compared to that obtained by a thermionic emission electron gun (e.g., $LaB_6$ electron gun) can be obtained, and a shot noise of the electron beam is quite large and inevitably an S/N ratio is not so good, which makes it difficult to evaluate a sample with high throughput.

On the other hand, the crossover image demagnification type beam by using the $LaB_6$ electron gun also has a drawback such that it is impossible to make the beam current higher, and this makes it difficult to evaluate a sample with high throughput.

Further, in the method for shaping a beam by using the $LaB_6$ electron gun, since it uses three or more stage of lenses, a long optical column must be used and a deflector is additionally required for axial alignment. It is also problematic that the space charge effect becomes greater in proportion to the length of the optical path, and it is difficult to accomplish a good intensity and position stability of the electron beam.

One of the subjects to be accomplished by the invention is to provide an electron beam system that can provide an evaluation of a sample with high throughput by reducing a shot noise of an electron beam and thereby improving the S/N ratio.

Another subject to be accomplished by the present invention is to provide an electron beam system that allows a beam current to be made higher and thus can evaluate a sample with high throughput.

Still another subject to be accomplished by the present invention is to provide a fully furnished system for a defect inspection apparatus by manufacturing an electron optical column employing only two stage of lenses to form and control a shaped beam with high stability.

Yet another subject to be accomplished by the present invention is to provide a manufacturing method of a device, in which a sample after having been processed is evaluated by using the electron beam system as described above.

An electron beam system according to the prior art is associated with the problems stated above, in addition to the problem that the system tends to be too complicated, and also that since the filter made up of hemispherical mesh used in a measurement of the potential contrast forms a non-axisymmetric electric field, an uncorrectable distortion may be induced in a measured result. Besides, since the electron gun of the schottky cathode type produces a big shot noise, it is required to apply a high beam current or to emit an intensified primary electron beam in order to obtain a good SIN ratio. Further, if the magnified crossover image is used as the above-stated probe current and an electron gun having the same intensity is used in this case, then again, problematically, the beam current would be smaller as compared to a case in using the demagnified image of the shaping aperture.

The present invention has been made to solve the problems pointed out above, and the object thereof is to provide an electron beam system which comprises an axisymmetric filter as well as an electron gun with a smaller shot noise, and allows a relatively higher beam current to be obtained as compared to that which can be achieved by using an electron gun with the same brightness, and also to provide a defect inspection method using the same electron beam system, as well as a device manufacturing method using the same electron beam system and defect inspection method.

There has been a problem that if both rough alignment and fine alignment are carried out, it takes a long time to complete an alignment operation, resulting in a lower throughput (a quantity of processing per unit time) achieved by the inspection apparatus. In addition, when an electron optical system is used to conduct alignment, an electron beam dose equivalent to or greater than that applied in the sample evaluation would be applied to the wafer, which in turn could destroy a gate oxide or the like. The present invention is also directed to solving the above problem. Accordingly, another object of the present invention is to provide an inspection apparatus, in which inspection of a wafer can be carried out by conducting alignment without using any electron beams, and thus without destroying the gate oxide and the like. Another object of the present invention is to provide a device manufacturing method using such an inspection apparatus as described above.

The above-described subjects are solved by the following means. That is, the present invention provides an electron beam system, in which an electron beam emitted from an electron gun is irradiated onto a sample and secondary electrons emanated from the sample are detected, wherein said electron gun is specified to be a thermionic emission electron gun, and a shaping aperture and a NA aperture are arranged in front locations of said thermionic emission electron gun, wherein an image of the shaping aperture irradiated by the electron beam from said thermionic emission electron gun is formed on a surface of the sample by two-stage lenses. It is to be noted that the expression "in (a) front location(s) of" is defined as in the sample side which is (are) in a forward side with respect to the direction along which the electrons advance. A secondary electron beam includes a reflected electron reflected by the sample surface, a transmission electron having transmitted through the sample, and an emanated electron emanated from the sample by the irradiation of the primary electron beam.

Further, according to one aspect of the present invention, there is provided an electron beam system in which an electron beam emitted from an electron gun is irradiated onto a sample and secondary electrons emanated from the sample are detected, wherein said electron gun is specified to be a thermionic emission electron gun and a shaping aperture and a NA aperture are arranged in front locations of said thermionic emission electron gun, wherein a crossover image formed by the electron beam from the thermionic electron gun is formed into an image in the NA aperture, and an image of the shaping aperture irradiated by the electron beam from the thermionic emission electron gun is formed on a surface of the sample.

Further, according to another aspect of the present invention, there is provided an electron beam system which has a primary optical system for irradiating an electron beam emitted from the electron gun onto a sample and in which secondary electrons emanated from a surface of the sample are detected by a detector, the system being characterized in that a shaping aperture and two-stage lenses are arranged in the primary optical system, and additionally, an E×B separator is arranged between the two-atage lenses, wherein an image of a shaping aperture irradiated by an electron beam from said electron gun is demagnified and formed on the sample surface by the two-stage lenses and secondary electrons emanated from the sample surface are separated by said E×B separator from the primary optical system and introduced into a detector.

According to still another aspect of the present invention, there is provided an electron beam system which has a primary optical system for irradiating an electron beam emitted from an electron gun onto a sample and in which secondary electrons emanated from a surface of the sample are detected by a detector, the system being characterized in that the primary optical system comprises a shaping aperture, a NA aperture, a condenser lens and an objective lens disposed in a sequential manner along an optical axis of the primary optical system, wherein a crossover image of the electron beam from the electron gun is focused to the NA aperture by controlling a Wehnelt bias (an electrode bias) of the electron gun.

According to yet another aspect of the present invention, provided is an electron beam system which has a primary optical system for irradiating an electron beam emitted from an electron gun onto a sample and in which secondary electrons emanated from a surface of the sample are detected by a detector, the system being characterized in that the primary optical system comprises a shaping aperture, a condenser lens and an objective lens disposed in a sequential manner along an optical axis of the primary optical system, and a NA aperture is disposed in a location adjacent to the objective lens in the electron gun side with respect to the objective lens, wherein a crossover image of the electron beam is formed in the NA aperture.

According to still another aspect of the present invention, there is provided a defect inspection apparatus for a device, which is equipped with an electron beam system as defined according to any one of the above-described inventions or other inventions. Further, according to the present invention, there is provided a device manufacturing method in which a wafer after having been processed is evaluated by using the above described defect inspection apparatus.

An electron beam system according to the present invention scans a sample surface by a primary electron beam emitted from an electron gun and then detects a secondary electron beam emanated from the sample. In this electron beam system, an objective lens is arranged for focusing the primary electron beam and for accelerating the secondary electron beam, wherein the objective lens has a plurality of electrodes. Preferably, the electron gun is operated in a space charge limited condition, meaning that a shot noise reduction coefficient is smaller than 1, and a voltage applied to a plurality of electrodes of the objective lens can be set to a desired value. Further, a demagnification ratio of the electron beam can be changed between a case for irradiating the electron beam against the sample so as to form a topographical or a material image of the sample surface, and another case for measuring a potential of a pattern formed on the sample.

Whether or not the electron gun operates in the space charge limited zone (condition) can be examined by referring to the attached drawings, FIGS. 14(a) and 14(b) and by using a method described below. FIG. 14(a) is a graph illustrating a relationship between an electron gun current and a cathode heating current, wherein in zone P, the electron gun current increase only by a small amount even if the cathode heating current is increased, which means that the zone P corresponds to the space charge limited condition. FIG. 14(b) is a graph illustrating a relationship between the electron gun current and an anode voltage, wherein in zone Q, the electron gun current increases sharply when the anode voltage is increased, which means that the zone Q also corresponds to the space charge limited condition. From the above description, it can be determined that the electron gun is operating in the space charge limited condition either when the cathode heating current is increased to measure the electron gun current thereby determining the P zone where the electron gun current is saturated, or when the anode voltage is increased to measure the electron gun current thereby determining the Q zone where the electron gun current is changing sharply. Accordingly, it is possible to set the condition for operating the electron gun in the space charge limited condition.

A defect inspection method using an electron beam system according to the present invention comprises: an image acquiring step for irradiating an electron beam emitted from the electron gun against the sample via the objective lens to obtain an image of a sample surface; a measuring step for measuring a potential or a variation thereof on the surface of the sample, which has been induced by irradiation of the electron beam; and a determining step for determining whether a specific pattern is good or not based on the potential or a variation thereof. In the image acquiring step and the measuring step, a voltage to be applied to an electrode most proximal to the sample among the plurality of electrodes of the objective lens may be changed.

Preferably, a defect inspection method of the present invention comprises: a step for forming an SEM image by the scanning, and then measuring and storing a position of a specific pattern on the sample; and a measuring step for measuring a potential of the pattern by the selective scanning or irradiation on said specific pattern, wherein it is examined from a result of measurement of the potential of the specific pattern whether or not there is a defect in the sample.

Preferably, a defect inspection method of the present invention comprises a step for acquiring an SEM image by the scanning and a step for measuring a potential of a pattern, wherein in the acquiring step and the measuring step, at least one of an excitation voltage of the objective lens, a landing voltage (energy) to the sample and a cathode voltage of the electron gun may be changed. The present invention further provides a device manufacturing method in which a wafer is evaluated at the end of each one of the processes for manufacturing the wafer by using either the electron beam system or the defect inspection method described above.

An inspection apparatus for evaluating a fine geometry on a surface of a sample according to the present invention comprises: an electron optical system including a primary optical system for irradiating an electron beam against a sample and a detecting system for detecting the electron beam emanated from the sample; a movable stage for carrying the sample and moving the sample relative to the electron optical system; and a position sensor capable of measuring a position of the sample with a desired precision. The position sensor is disposed in a location spaced by a desired distance from the electron optical system, and the movable stage is moved on the basis of a position signal output from the position sensor so as to bring the sample into a reference position in said electron optical system with a desired precision. The inspection apparatus, in the condition where the sample has been matched to the reference position in the electron optical system with the desired precision, acquires an SEM image of a surface of the sample by the electron optical system and the thus acquired SEM image is compared to another acquired SEM image or to a reference image for the pattern matching, thereby allowing for competitive evaluation.

In the present invention, preferably, comparative evaluation is conducted by applying a pattern matching between an SEM image acquired from one segment on one sample and another SEM image acquired from a corresponding segment on a different sample. Alternatively, the SEM image acquired from one segment on one sample may be compared with a reference image for the pattern matching, thus carrying out the comparative evaluation. The position sensor measures the position of the sample by measuring an electrostatic capacity. Further, in an inspection apparatus of the present invention, pattern matching is applied between the SEM image and the reference image to provide a comparative evaluation by performing one of translation, rotation or magnification tuning of the image.

An inspection apparatus for evaluating a fine geometry on a surface of a sample according to the present invention comprises: an electron optical system consisting of a primary optical system for irradiating an electron beam against the sample and a detecting system for detecting an electron beam emanated from the sample; a movable stage for carrying and moving the sample relatively with respect to the electron optical system; and a position sensor disposed in a location spaced by a predetermined distance from the electron optical system and being capable of measuring the position of the sample with a desired precision. In the inspection apparatus of the present invention, the movable stage is actuated on the basis of a position signal output from the position sensor to bring the sample into a reference position in the electron optical system. The inspection apparatus, in a condition that the sample has been matched to the reference position in the electron optical system with a desired precision, acquires an SEM image of a surface of the sample by the electron optical system, calculates a difference between an area to be evaluated on the sample surface and a field of view of the electron optical system based on the acquired SEM image, and then corrects the thus calculated difference by the deflector so as to acquire the SEM image.

Further, in an inspection apparatus of the present invention, pattern matching is applied between the SEM image and the reference image to provide a comparative evaluation by performing one of translation, rotation or magnification tuning of the image. In a device manufacturing method of the present invention, a wafer in the course of processing is evaluated by using one of the inspection apparatuses as described above.

BRIEF DESCRIPTION OF THE DRAWINGS

FIG. 10*a* is an SEM image including a field of view 521 acquired by an electron optical system while FIG. 10*b* is a reference image including a field of view 522, and FIG. 10*c* is a plan view showing an example of a corner of a pattern;

FIG. 13*a* is a plan view showing a physical relationship between an electrode of a position sensor and a wafer, while FIG. 13*b* is a side view showing a physical relationship between the electrode of the position sensor and the wafer as well as a block diagram of respective components; and FIG. 14*a* is a graph illustrating a relationship between an electron gun current and a cathode current, while FIG. 14*b* is a graph illustrating a relationship between an electron gun current and an anode voltage.

EXPLANATION OF REFERENCE SIGNS

Th components and elements used herein are designated as follows:

1, 1': Electron beam system, 10, 10': Primary optical system, 11: Electron gun, 12: Electrostatic deflector (for axial alignment), 13: Shaping aperture, 14, 15: Electrostatic deflector (for axial alignment), 16: NA aperture, 17: Condenser lens, 18: Electrostatic deflector, 19: E×B separator, 20: Objective lens, 21: Axisymmetric electrode, 22, 23: Power supply, 24: Shift switch, 25: Electrostatic deflector, 30: Secondary optical system, 40, 40': Detector, 71: Optical column, 73: XY stage, 74: X table, 77: Y table, 83: Linear motor, 87: Irradiation space, 91: Flexible pipe, 98: Exhaust pipe, 201: Cathode, 202: Wehnelt, 203: Anode, 204: First condenser lens, 205: Second aperture plate, 206: First aperture plate, 207: Second condenser lens, 208: Objective lens, 210: E×B separator, 211: Shield barrel, 212: Secondary electron detector, X: Optical axis, 401, 401': detector, 402: A/D converter, 403: Image processing circuit, 502*a*, 502*b*, 502*c*, 505: Electrostatic capacity sensor, 503: Periphery, 504: Notch, 510, 521, 522: Field of view, 525-528: Pattern corner of SEM image, 525'-528': Pattern corner of reference image, 529: Defect, 531: Arc, 535: Optical axis, 536: Primary optical system, 538: Detecting system, 539: Optical axis, 540: Position sensor, 541: Electrode, 542: Overlapped portion, 546: Electrostatic capacity measuring instrument, 547: Comparison chart, 548: Position detector, 600: Electron beam system, 601: Electron gun, 603: Condenser lens, 607: First multi-aperture plate, 609: Demagnifying lens, 610: Narrow gap, 615: Sample, 619: E×B separator, 623, 625: Magnifying lens, 627: Second multi-aperture plate, 629: Detector, 631: Amplifier, 628: Stop, 633: Image processing section, 635: Deflector, 637: Knife edge, 639: Am meter, 643: CPU, 645: Storage, 649: Output means, A, B, P: Optical axis, C: Electron beam, G: Center of gravity of wafer, and S: Sample (Wafer).

EMBODIMENTS OF THE INVENTION

Figure 1:
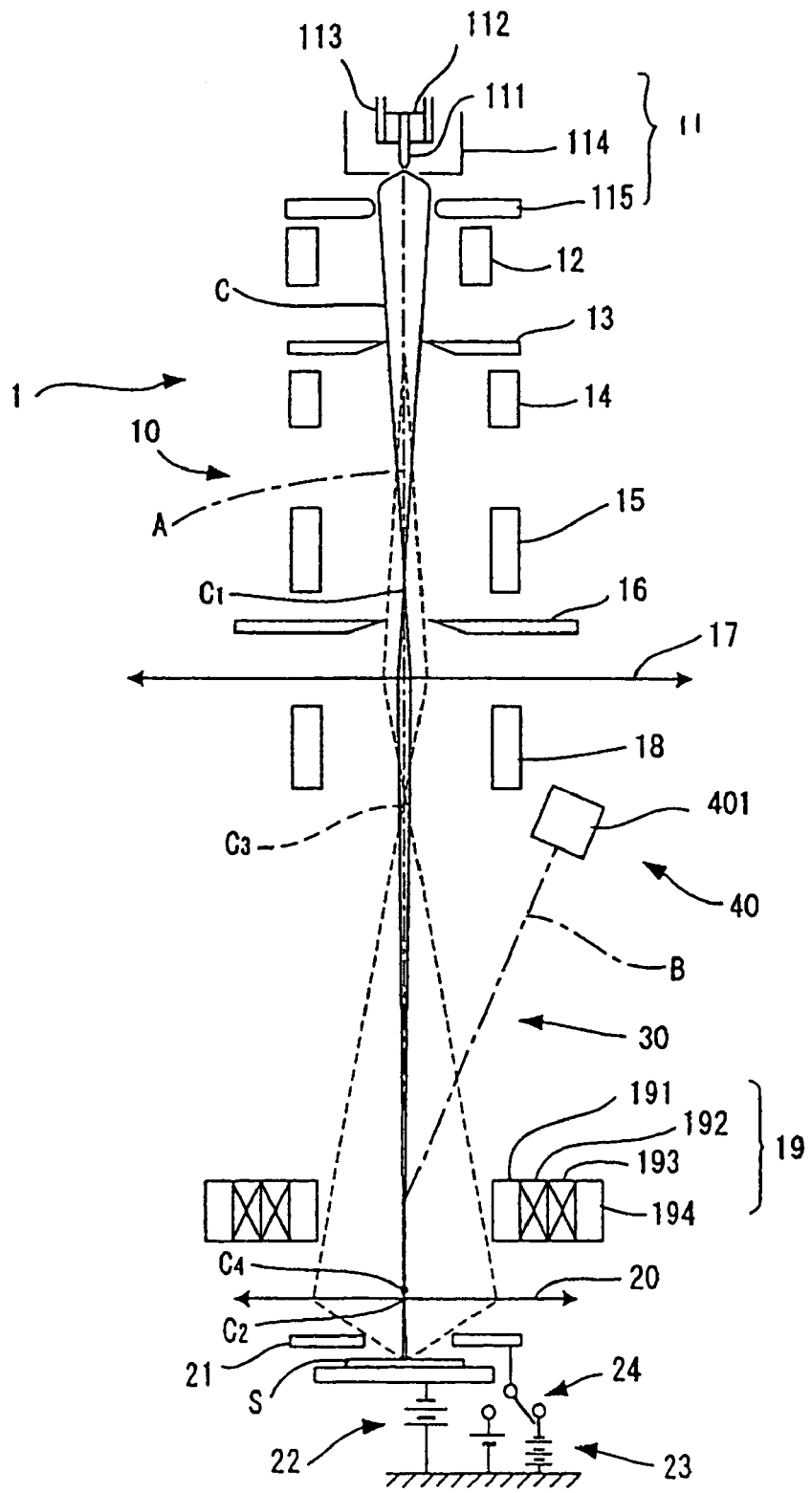
FIG. 1 is a general schematic diagram of an optical system of an electron beam system according to a first embodiment of the present invention.

A first embodiment of an electron beam system according to the present invention will now be described in detail with reference to the attached drawings. FIG. 1 schematically shows an electron beam system 1 according to a first embodiment of the present invention. This electron beam system 1 comprises a primary optical system 10, a secondary optical system 30 and a detecting system 40. The primary optical system 10 serves as an optical system for irradiating an electron beam onto a sample "S", and comprises an electron gun 11 for emitting the electron beam, an electrostatic deflector 12 used for an axial alignment, a shaping aperture 13, electrostatic deflectors 14, 15 used for the axial alignment, a NA aperture, a condenser lens 17 for demgnifying the electron beam after passing through the shaping aperture 13, an electrostatic deflector 18 used for scanning, an E×B separator 19, an objective lens 20 and an axisymmetric electrode 21, all of which are arranged in a sequential manner with the electron gun 11 placed at the topmost location in a manner such that an optical axis "A" of the electron beam emitted from the electron gun may be normal to a surface "S" of the sample. The E×B separator 19 is constituted of an electrostatic deflector 191, electromagnetic deflectors 192, 193 and a permalloy core 194. The electron beam system 1 further comprises a power supply 22 for applying a negative potential to the sample S.

In the first embodiment, the electron gun 11 is implemented as a $LaB_6$ electron gun of the thermionic emission type, which comprises a $LaB_6$ cathode 111, a graphite heater 112, a support fittings 113, a Wehnelt electrode 114 and an anode 115. By adjusting a bias of the Wehnelt electrode 114 of the electron gun 11 to be deeper to some extent, the electron gun 11 can be controlled within a space charge limited condition. The shaping aperture 13 is square in shape and disposed in a location in the electron gun side with respect to the NA aperture 16. Further, both of the two-stage lenses (i.e., the condenser lens 17 and the objective lens 20) are disposed in front locations of the shaping aperture 13 and the NA aperture 16 (i.e., in the sample side which is in a forward side with respect to the direction along which the electron beam advances).

The secondary optical system 30 is serving as an optical system for introducing secondary electrons emanated from the sample S into the detector 40, and disposed along the optical axis "B" angled with respect to the optical axis "A", starting from a point proximal to the E×B separator 19. The detecting system 40 comprises a detector 401.

An operation of the electron beam system 1 configured as stated above will now be described.

An electron beam "C" emitted from the electron gun 11 may form a crossover image "$C_1$" in a location corresponding to that of the NA aperture 16 by adjusting the Wehnelt voltage of the electron gun 11. At the same time, the electron gun 11 is controlled so as to operate within the space charge limited condition by adjusting a current to be applied to the graphite heater 112. Accordingly, this can reduce a shot noise induced by the electron beam to be significantly low. The electron beam, which has formed the crossover image $C_1$, is dispersed at a not-so-big spreading angle and then focused by the condenser lens 17 so as to form a crossover image "$C_2$" in a location on a principal plane of the objective lens 20. In this case, an excitation voltage of the condenser lens 17 is determined so that the electron beam can form the crossover image $C_2$ in the location on the principal plane of the objective lens 20.

On the other hand, an image of the shaping aperture 13 formed by the electron beam is demagnified by the condenser lens 17 into the image in a location "$C_3$", and further demagnified by the objective lens into the image of 0.1 μm or smaller on the surface of the sample S. This adjustment can be performed easily by changing the excitation voltage of the condenser lens 17.

For scanning the sample, the electrostatic deflector 18 and the electrostatic deflector 191 of the E×B separator are used so as to provide the scanning operation by way of a two-stage deflection. In this case, a total value of a deflection chromatic aberration, a coma aberration and an astigmatism may be minimized by setting a center of deflection in a location "$C_4$" directly above the objective lens 20.

The sample S is irradiated by the electron beam, and the secondary electrons emanated from the sample are accelerated and converged in an accelerating electric field of the objective lens 20 and deflected by the E×B separator 19 to be introduced into the secondary optical system 30. In this case, normally, since a negative voltage has been applied to the sample S by the power supply 22, almost all of the secondary electrons can pass through the objective lens 20 so as to be deflected by the E×B separator 19. The secondary electrons are moved along the optical axis B and detected by the detector 401.

It is to be noted that such an arrangement may be employed in which the axisymmetric electrode 21 is disposed in the sample side with respect to the objective lens 20, and a power supply 23 and its associated shift switch 24 for applying a positive or a negative voltage to this axisymmetric electrode 21 are provided, so that the axisymmetric electrode 21 may be controlled to have a filtering function by applying thereto a lower voltage than that of the sample. In such a case, a potential contrast of the pattern on the sample surface can be obtained.

Further, it may become possible to carry out defect inspection with high precision by obtaining a normal image of the scanning electron microscope or by obtaining a potential contrast image through control of the shift switch 24 by using a computer. Consequently, the electron beam system according to the present invention is applicable to a defect inspection apparatus for a device.

Figure 2:
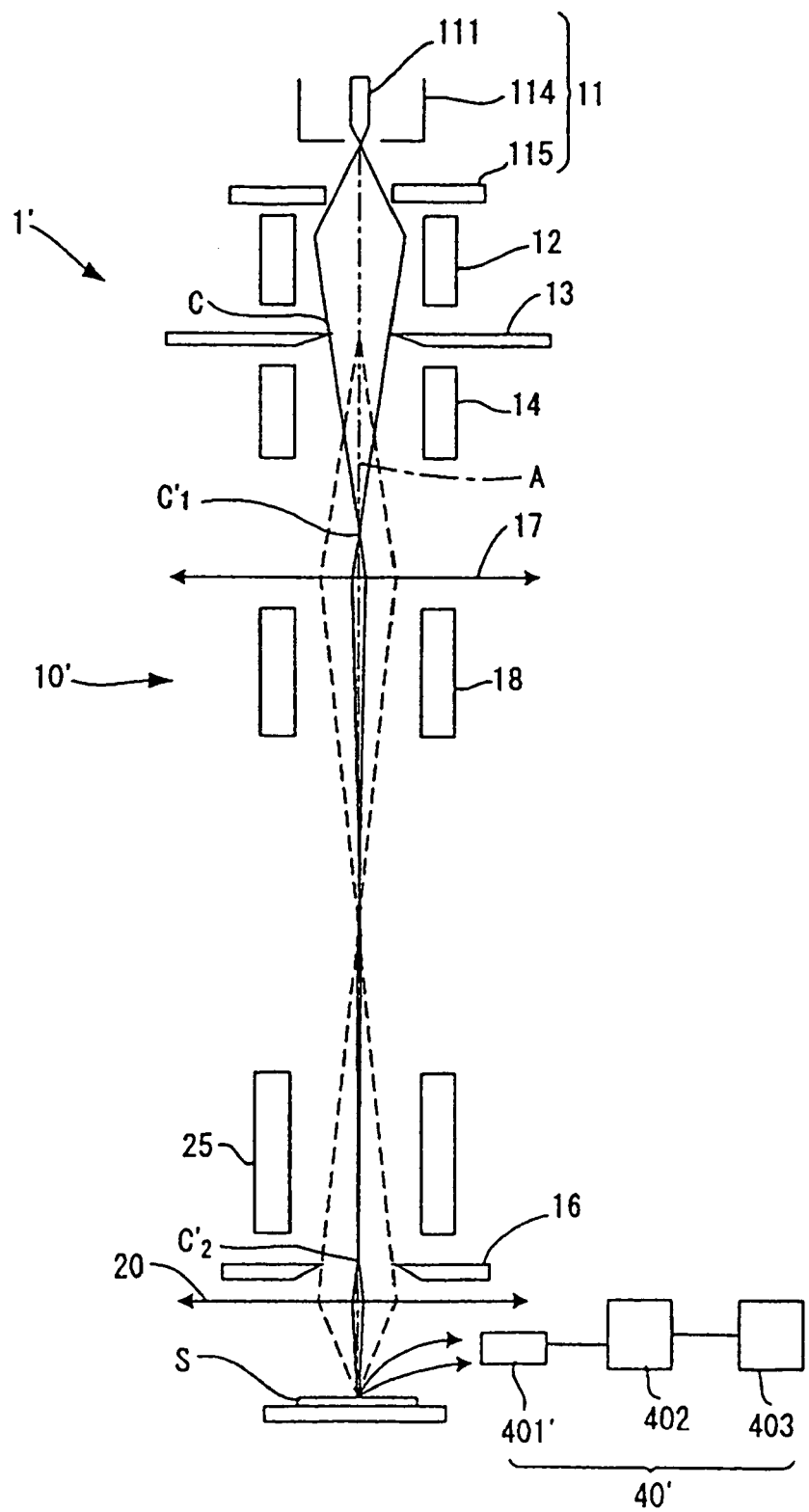
FIG. 2 is a general schematic diagram of an optical system of an electron beam system according to a second embodiment of the present invention.

An electron beam system 1' according to a second embodiment of the present invention will now be described with reference to FIG. 2. In this drawing, the same components as those in the first embodiment shown in FIG. 1 are designated by the same reference numerals. Further, components corresponding to but different from components specified in the first embodiment are designated by the same reference numerals and denoted with a symbol "'". The electron beam system 1' according to the second embodiment, is different from that in the first embodiment, only in that it comprises a primary optical system 10' and a detecting system 40'. The primary optical system 10' comprises an electron gun 11 having a similar configuration to that in the first embodiment, an electrostatic deflector 12 for axial alignment, a shaping aperture 13, an electrostatic deflector 14 for an axial alignment, a condenser lens 17 for condensing an electron beam after it has passed through the shaping aperture 13, electrostatic deflectors 18, 25 for scanning, a NA aperture 16 and an objective lens 20, all of which are disposed appropriately with the electron gun 11 placed at a topmost location in such a manner that an optical axis "A" of the electron beam emitted from the electron gun 11 may be normal to a surface "S" of a sample.

The electron gun 11 in this second embodiment can also be controlled within a space charge limited condition by adjusting a bias of a Wehnelt electrode to be deeper to some extent. As clearly shown in FIG. 2, the NA aperture 16 is disposed adjacent to the objective lens 20 in the electron gun side with respect to the objective lens 20. Further, differently from the first embodiment, the axial aligning electrostatic deflector is implemented as a two-stage configuration and no E×B separator nor axisymmetric electrode is provided. In the second embodiment, a secondary optical system is not provided for its own purpose, but secondary electrons emanated from the sample S are attracted by an electric field of a detector 401' of the detecting system 40' to be introduced directly into the detector 401', which will be explained later. The detecting system 40' comprises the detector 401', an A/D converter 402 and an image processing circuit 403.

An operation of the electron beam system having the configuration designated above according to the second embodiment will now be described. An electron beam "C" emitted from the electron gun 11 passes through the shaping aperture 13 to form a crossover image "$C_1$'" in a predetermined location between the shaping aperture 13 and the condenser lens 17, and then the beam is dispersed from the crossover image $C_1$' at a spreading angle that is not too great.

The dispersed electron beam is converged by the condenser lens 17 to form a crossover image "$C_2'$" in the NA aperture 16. After forming the crossover image $C_2'$, the electron beam proceeds toward the sample S and is directed to the sample S by the objective lens 20. An image of the shaping aperture 13 is demagnified by the condenser lens 17 and the objective lens 20 into the image on the sample S. In order to scan the sample, the beam is deflected in a two-stage manner by using the electrostatic deflector 18 and the electrostatic deflector 25 for scanning.

The secondary electrons emanated from the sample S by the irradiation of the electron beam onto the sample S is deflected by the electric field of the deflector 401' so as to be introduced into the deflector 401'. The deflector 401' converts the detected secondary electron into an electric signal indicative of intensity of the secondary electron. The electric signal output from the detector 401' is converted by the A/D converter 402 into a digital signal and is then received by the image processing circuit 403, where the digital signal is converted to image data. This image is compared to the reference pattern, and thereby any defects in the sample S can be detected. Accordingly, the electron beam system of the second embodiment is also applicable to the defect inspection apparatus for a device.

The electron beam systems according to the first and the second embodiments can be used to evaluate the sample after having been finished with those processes in a semiconductor device manufacturing method, which will be described later with reference to FIG. 7 and FIG. 8. Applying the electron beam system of the present invention to a testing process in the manufacturing method for the semiconductor device enables such a semiconductor device having a fine pattern to be inspected with high throughput, thereby allowing for 100% inspection, thus improving an yield of the product and preventing the shipment of any defective products.

Figure 3:
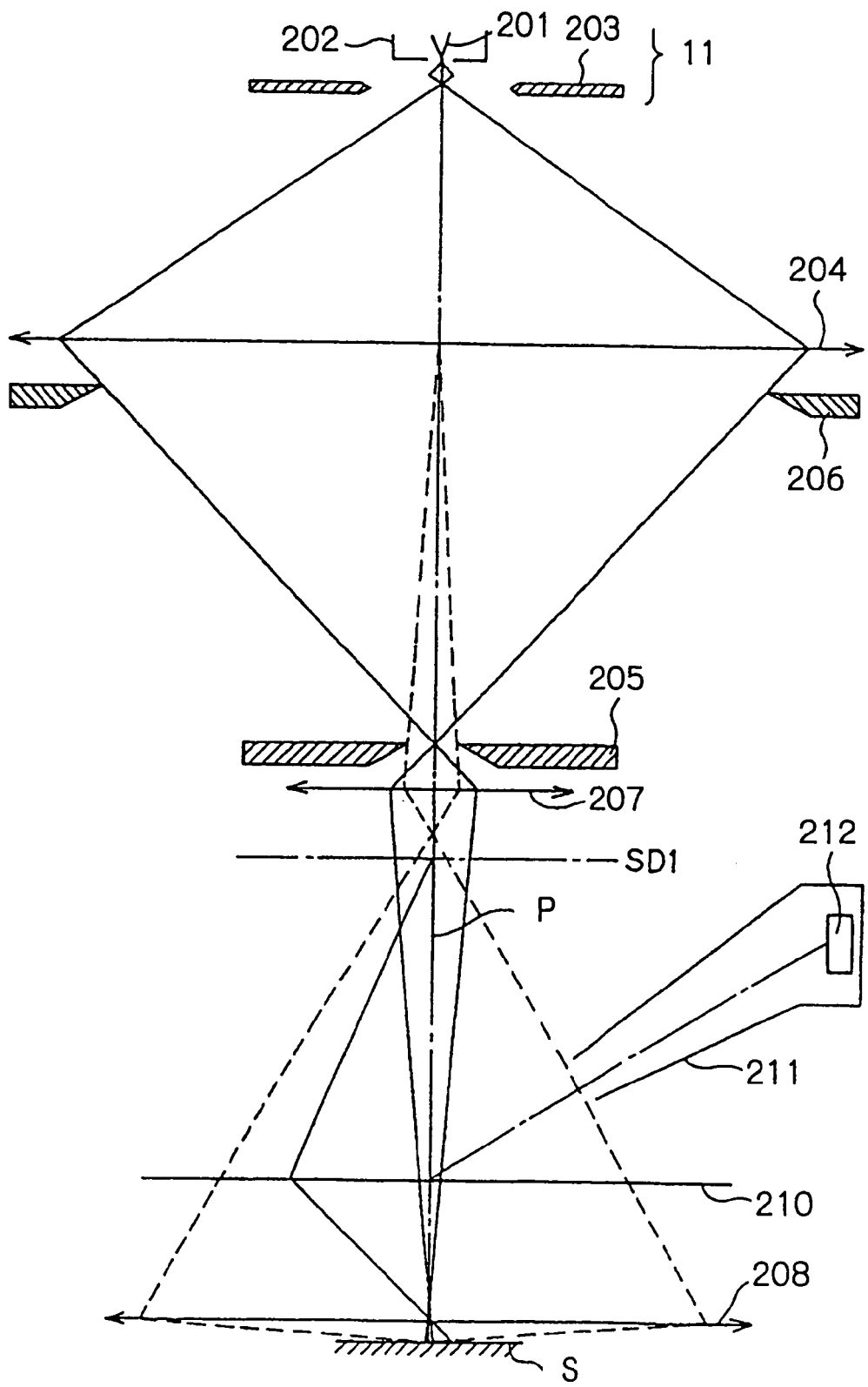
FIG. 3 is a schematic diagram of one exemplary configuration of an electron optical system in an electron beam system according to the present invention.

Some further embodiments of the present invention will now be described below with reference to FIG. 3 to FIG. 6. FIG. 3 shows one example of configuration of an electron optical system in an electron beam system according to a third embodiment of the present invention. In FIG. 3, an electron gun 11 comprises a cathode 201 made of $LaB_6$ single crystal, a Wehnelt 202 and an anode 203, which are operated within a space charge limited condition. A primary electron beam emitted from the electron gun 11 is converged by a first condenser lens 204 to form a crossover image in a second aperture plate 205. A first aperture plate 206 has a square opening and thereby enables a high beam current (an intensified primary electron beam) to be obtained. It is to be noted that if a slightly deteriorated resolution in any specific direction is permissible, then a rectangular opening, instead of the square opening, may be used. The first aperture plate 206 having a shaping aperture is disposed downstream to the first condenser lens 204, and a primary electron beam after passing through the first aperture plate 206 is demagnified to be ¹⁄₁₀₀ in scale with the aid of a second condenser lens 207 and an objective lens 208 so as to form an image on a sample "S", such as a wafer. It is to be noted that reference symbol "SD1" designates a first scanning deflector and "P" designates an optical axis of the optical system.

In this third embodiment, the objective lens 208 may be, for example, an electrostatic lens having three pieces of electrodes axisymmetric with respect to the optical axis P. One among three electrodes, which is disposed in the electron gun side, is controlled to have a voltage proximal to the ground, which will be changed to provide dynamic focusing, thereby correcting an image field curvature aberration or a fluctuation in height of the sample surface during a movement of a stage. A central electrode is applied with a positive high voltage, and this can enhance a focusing action for the primary electron beam and reduce an axial chromatic aberration. On the other hand, a secondary electron beam emanated from the sample S is accelerated by the acceleration field produced by the electrodes of the objective lens 208, and all of the secondary electrons pass through the objective lens 208 when a topographical image or a material image of the sample surface is to be formed. That is, at least two electrodes are adapted to have desired voltages applied thereto. Ideally, three of the electrodes may be preferably controlled to have desired voltages, respectively. Employing such axisymmetric electrodes would not produce a non-axisymmetric electric field, thereby preventing any additional aberration from being generated.

An E×B separator 210 is disposed upstream to the objective lens 208, and this E×B separator 210 deflects the secondary electron beam off from the optical axis of the primary optical system (to deflect it toward the right hand direction on the paper in FIG. 3). The deflected secondary electron beam passes through a shielded pipe 211 and then it is detected by a secondary electron detector 212.

Measuring a noise contained in a signal detected by the secondary electron detector 212 makes it possible to determine whether or not the electron gun 11 made of $LaB_6$ single crystal is operating in the space charge limited condition. That is, assuming the shot noise is denoted by "N" and expressed in the following equation:

$$N^2 = \Gamma^2 e I_e \Delta f,$$

if the "Γ" is smaller than 1, it is determined that the electron gun 11 is operating in the space charge limited condition. Wherein, the "Γ" is a shot noise reduction coefficient, the "e" represents a charge of an electron, the "$I_e$" represents a current detected by the secondary electron detector 212, and the "Δf" represents a band width in which the noise is measured. It is to be noted that preferably the Γ is equal to or less than 0.5, ideally equal to or less than 0.2.

In contrast to that the Γ=1 in the electron gun of schottky cathode type, since the present invention employs an electron gun operating in a space charge limited condition, a shot noise can be reduced by Γ times and thus a beam current $\Gamma^{-2}$ times high as that attainable by the prior art can be made available to obtain a signal with a desired S/N ratio, or a signal having the same S/N ratio can be obtained in a measuring time multiplied by $\Gamma^{-2}$.

In a fourth embodiment of the present invention, defect inspection is carried out by using the electron beam system comprising the electron optical system shown in FIG. 3, in which, for example, a electric resistance of a via connection with a lower-layer wiring may be evaluated, said via being used to connect the lower-layer wiring and an upper-layer wiring in a multi-layered wiring sample. Evaluating the electric resistance of the via connection with the lower-layer wiring takes advantage of such a characteristic that when the charge is given to the surface of the sample, if the lower-layer wiring is grounded or almost grounded and the electric resistance between the via connection and the lower-layer wiring is sufficiently small, then the via may immediately return back to the ground potential, but if the electric resistance between the via connection and the lower-layer wiring is great, then the via may be charged to positive. Accordingly, measuring the surface potential immediately after the injection of the charges to the sample by the electron beam system shown in FIG. 3 allows the electric resistance of the via connection with the lower-layer wiring to be evaluated. Further, measuring the changes in potential of the via over time can provide a more accurate measurement of the electric connection resistance, and also using the electron beam system of FIG. 3 to perform the defect inspection can improve the throughput.

Normally, the via has a cross sectional area as small as the minimum line width at a location along the surface of the lowest layer of the multi-layered wiring, and the cross sectional area thereof becomes gradually bigger toward the topmost layer. When the via has a greater sectional area, it may be better to use a greater diameter of the beam so that the defect inspection can be carried out at high rate. Accordingly, in the fourth embodiment, when the via having the larger diameter is to be evaluated, the position of the second aperture plate 205 of FIG. 3 along the optical axis may be changed and also the demagnified ratio of the beam from the first aperture plate 206 may be changed, thereby obtaining the beam having a desired diameter. Further, upon making the probe beam by forming a crossover enlarged image or demagnified image on the sample surface, the crossover reducing ratio should be changed.

Figure 4:
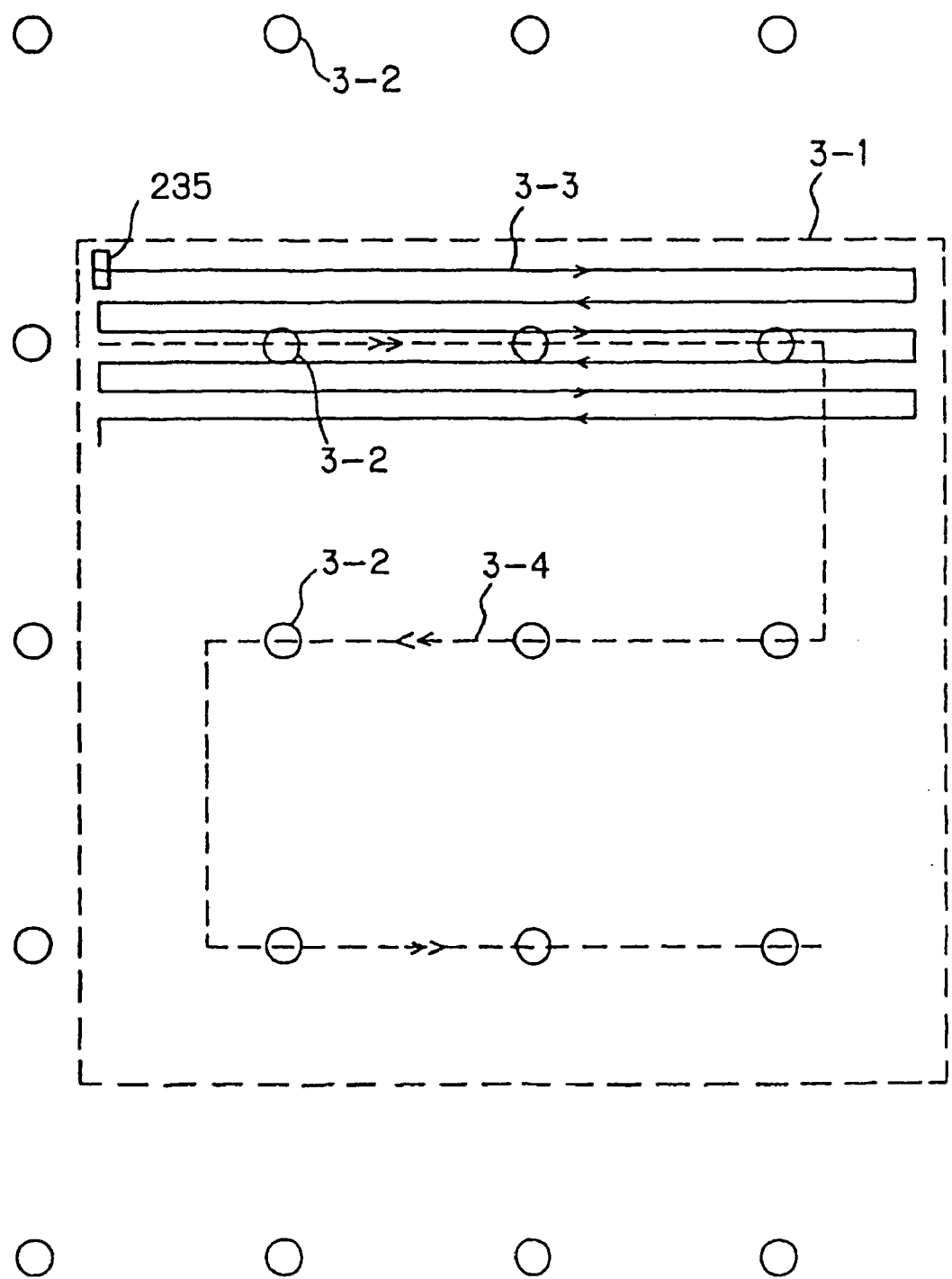
FIG. 4 is a diagram for illustrating a defect inspection carried out by using the electron beam system of FIG. 3.

Turning now to FIG. 4, how to apply the defect inspection to the via by using the electron beam system shown in FIG. 3 will now be described. A field of view for scanning by the electron beam system is indicated by a rectangular shape 3-1 of dotted line. The area within this field of view for scanning 3-1 is raster scanned along the solid line 3-3 by the electron beam system. The secondary electrons generated by this raster scanning are detected by the secondary electron detector 212 to obtain the SEM image. Since the secondary electron emission efficiency is higher in the location including a via 3-2 within the field of view for scanning 3-1, a brighter image can be acquired therein, which is then stored. This means that a different image would be obtained in dependence on the variation in the material of the sample surface. When the SEM image is to be obtained, since the ground voltage is being applied to the one electrode most proximal to the sample among those electrodes of the objective lens while the negative voltage is being applied to the sample S, therefore the secondary electrons are accelerated so as to be efficiently detected.

Figure 5:
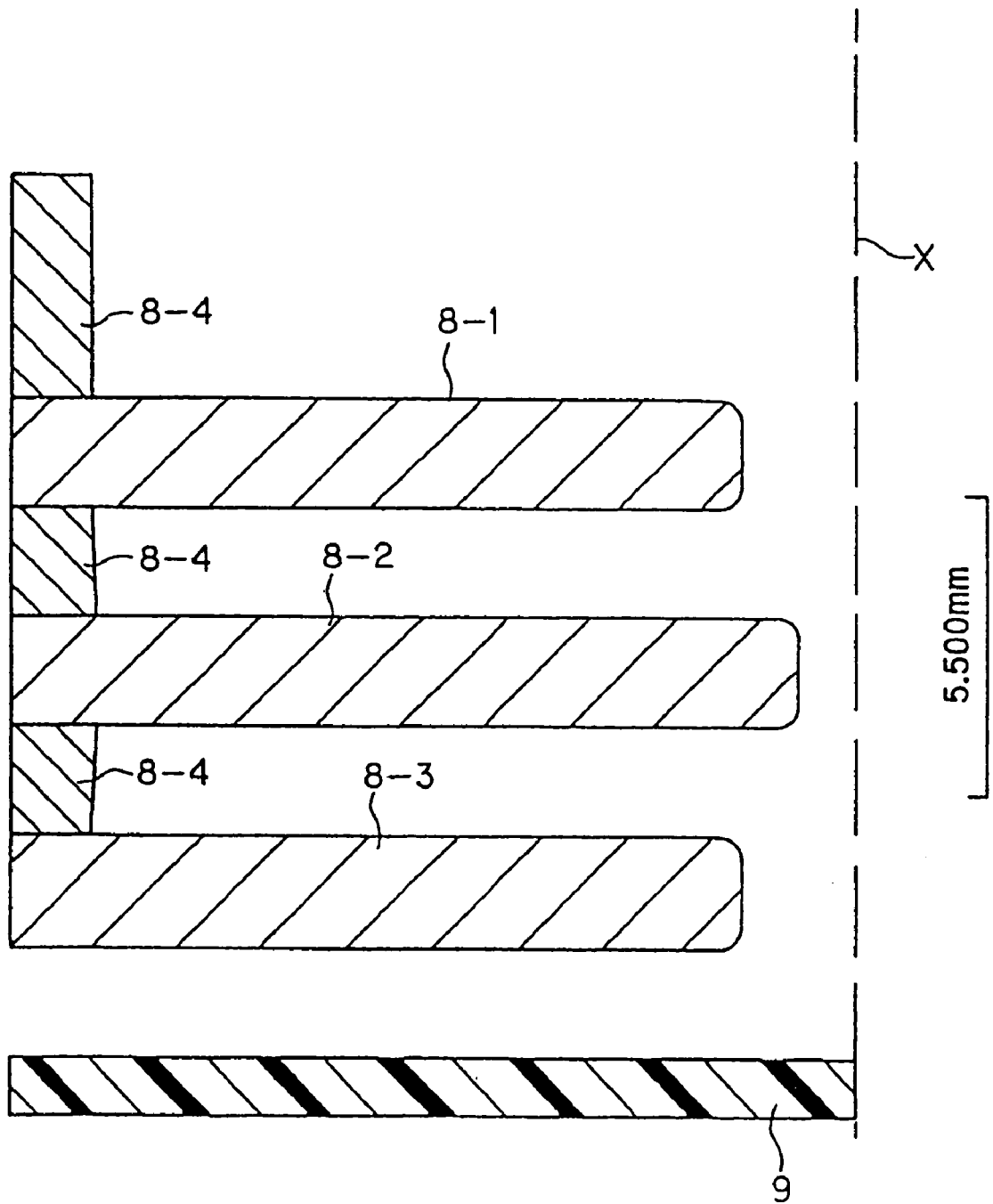
FIG. 5 is a sectional view showing a physical relationship between an objective lens and a sample in an electron beam system of FIG. 3, illustrating only a left half thereof with respect to an optical axis.

A fifth embodiment of the present invention relates to a technology for measuring a potential contrast by using the electron beam system shown in FIG. 3. FIG. 5 is a diagram illustrating specifically a physical relationship between the objective lens 208 of FIG. 3 and the sample S. It is to be noted that FIG. 5 shows only a left half of a cross section including the optical axis P of three electrodes of the objective lens 208, an upper electrode 8-1, a central electrode 8-2, and a lower electrode 8-3, as well as the sample S, so that a 3D figure formed by turning the cross section of the electrodes around the optical axis P shows an actual unit of electrodes. Reference numeral 8-4 designates insulating spacer for insulating the upper electrode 8-1, the central electrode 8-2 and the lower electrode 8-3 from each other. The thickness of each insulating spacer and the interval between the insulating spacers are both 2 mm, for example. If a voltage lower than that of the sample S is applied to this lower electrode 8-3 of the objective lens 8, the potential contrast for the pattern formed on the sample S can be measured. This will be described with reference to FIG. 6.

Figure 6:
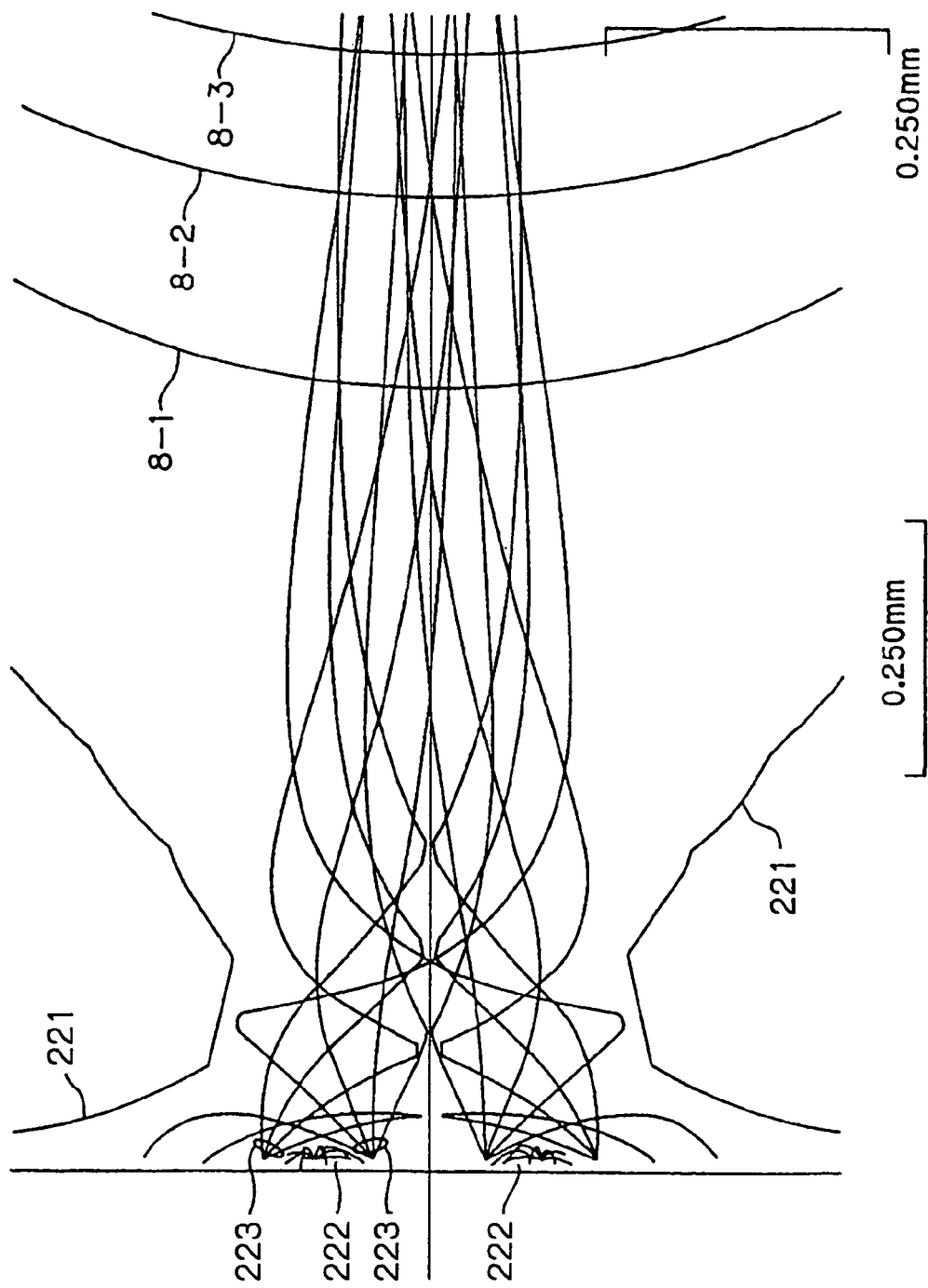
FIG. 6 is a diagram showing a simulation result indicative of the fact that a potential contrast can be measured by using the electron beam system of FIG. 3.

FIG. 6 shows a result of a simulation which shows that a potential contrast can be measured by this electron beam system, in which a voltage lower than that of the sample S by 300V is applied to the lower electrode 8-3 most proximal to the sample among the electrodes of the objective lens 208.

In FIG. 6, reference numeral 221 designates an equipotential surface of −1V, reference numeral 222 designates an trajectory of the secondary electron emitted from the pattern having a potential of 2V at an initial speed of 0.2 eV, and reference numeral 223 designates an trajectories of the secondary electron emitted from the pattern having a potential of 0V at an initial speed of 0.2 eV.

Is can been seen from FIG. 6 that the secondary electrons emitted from the pattern having the potential of 2V are returned back to the sample S side, but the secondary electrons emitted from the pattern having the potential of 0V passed through those three electrodes, the upper electrode 8-1, the central electrode 8-2 and the lower electrode 8-3. This indicates that those secondary electrons from the pattern having the potential of 0V can be detected, but those secondary electrons from the pattern having the potential of 2V cannot be detected, which means that the potential contrast can be measured.

A sixth embodiment of the present invention will now be described. When the potential contrast is to be measured, since the voltage lower than that of the sample S by approximately 300V is applied to the electrode most proximal to the sample S among those electrodes of the objective lens 208, the potential contrast can be obtained, but instead, an aberration characteristic of the objective lens 208 may be deteriorated, and if the beam is converged, then the beam current is apt to be smaller and thereby the S/N ratio may also become lower. As one solution to this problem, scanning may be skipped for the locations containing no via during measuring the potential contrast, as shown in 3-4. That is, only the locations containing vias should be selectively scanned. If the system is controlled to apply the irradiation only to the vias, then the measuring time would be further shortened. Besides, preferably, the geometry of the beam may be shorter in the scanning direction but may be longer in the direction normal to said scanning direction, as shown by 235 in FIG. 4. This ensures that the via may be scanned properly, even in the case of the slightly offset operational position. Such geometry of the beam may be formed through the aperture provided in the first aperture plate 205 of FIG. 3.

According to a seventh embodiment of the present invention, when a voltage applied to the electrode most proximal to the sample 8 among those electrodes of the objective lens 208, i.e., the lower electrode 8-3, is changed, depending on a case where the raster scan is carried out to obtain the SEM image or a case where the potential contrast is measured, the voltage applied to the central electrode representing the focusing condition in the sample S may be also changed.

It is to be appreciated that scanning for the purpose of giving charges to the sample S by the electron beam system shown in FIG. 3 may be carried out with an optimal landing energy, that is, a landing energy that can provide a desired potential with a least dose. Adjusting this landing energy can be performed by changing a cathode potential of the electron gun 11 and/or changing, a retarding voltage to be applied to the sample S.

Turning now to flowcharts in FIG. 7 and FIG. 8, a semiconductor device manufacturing method by using the electron beam system of the present invention will be described. The electron beam system of the present invention may be used to evaluate a wafer in the course of processing or after having been processed in the flowcharts of FIG. 7 and FIG. 8.

Figure 7:
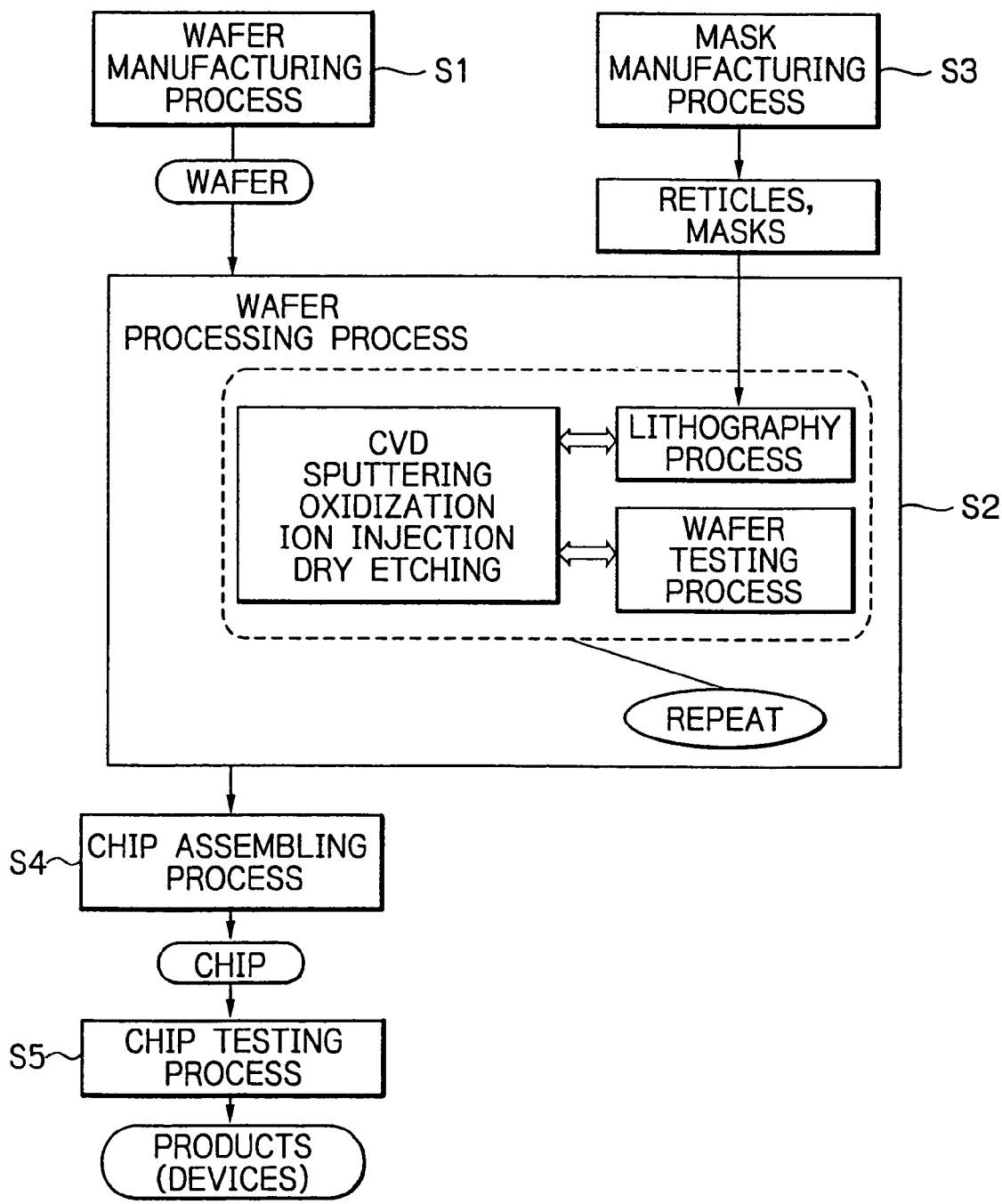
FIG. 7 is a flow chart of a method for manufacturing a semiconductor device by employing an electron beam system according to the present invention.

As shown in FIG. 7, the semiconductor device manufacturing method, if generally segmented, may comprise a wafer manufacturing process S1 for manufacturing a wafer, a wafer processing process S2 for providing any processing required for the wafer, a mask manufacturing process S3 for manufacturing the mask required for exposure, a chip assembling process S4 for cutting out those chips formed on the wafer one by one so as to make them operative, and a chip testing process S5 for testing the finished chips. Each of those processes includes some sub steps, respectively.

Among the processes described above, the process which may give critically effect semiconductor device manufacturing is the wafer processing process. The reason is that in this process, a designed circuit pattern is formed on the wafer and also a lot of chips are expected to operate as a memory, or a MPU are formed thereon.

Thus, it is important to evaluate the processed condition of the wafer representing the result of the processes executed in the sub steps of the wafer processing process which has much effect on the manufacturing of the semiconductor wafer, and those sub steps will be described below.

First of all, a dielectric thin film for functioning as an insulation layer is deposited, and a metal thin film is also deposited, which forms a wiring section and an electrode section. The film deposition may be performed by the CVD or the sputtering. Then, the deposited dielectric thin film and metal thin film together with the wafer substrate are oxidized, and also a resist pattern is formed in a lithography process by using a mask or reticle produced in the mask manufacturing process S3. Then, the substrate is processed according to the resist pattern by using the dry etching technology or the like, and ions or other impurities are implanted therein. After that step, the resist layer is removed, and the wafer is subjected to testing.

Such a wafer processing process as described above may be repeated by a desired number of layers to produce the wafer which in turn is separated into respective chips in the chip assembling process S4.

Figure 8:
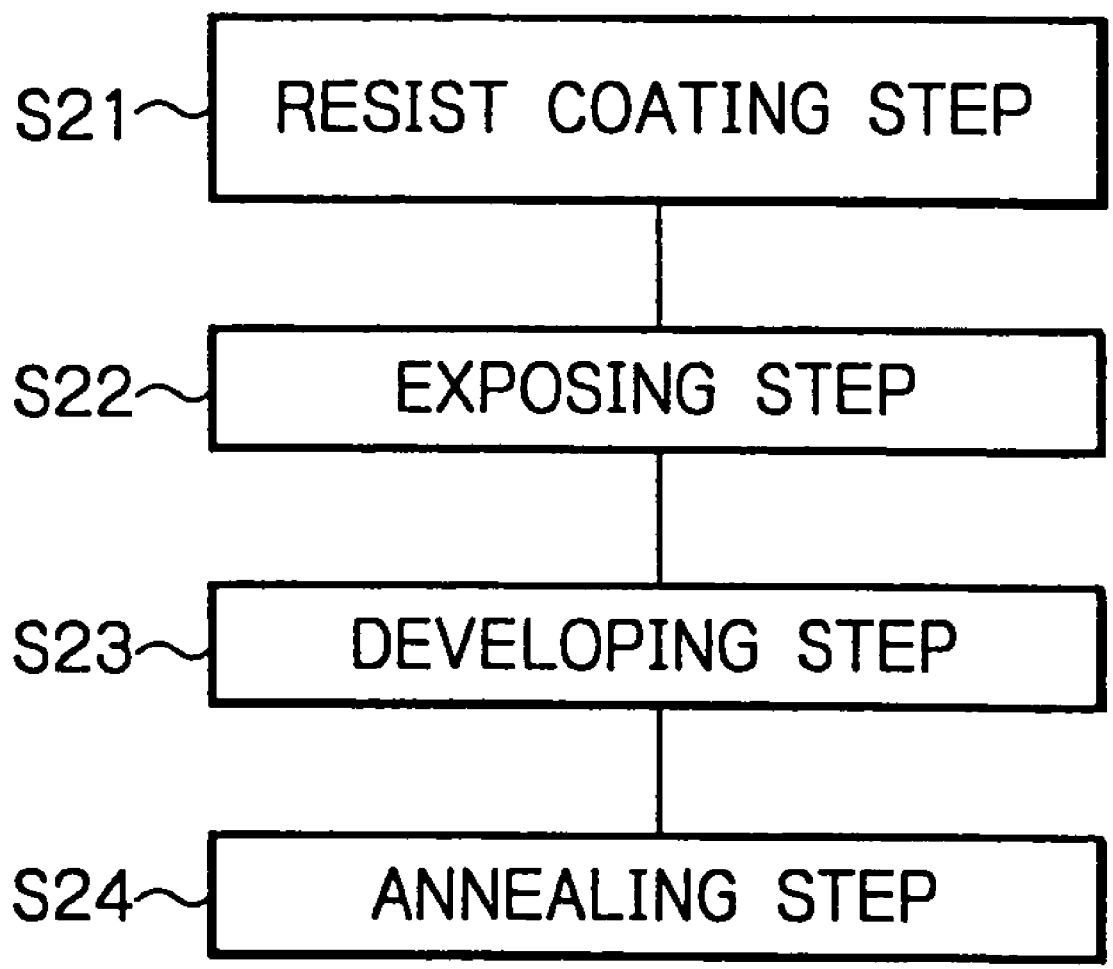
FIG. 8 is a flow chart of a lithography process included as a sub-process in a wafer processing process shown in FIG. 7.

FIG. 8 is a flow chart illustrating the lithography process included as a sub step in the wafer processing process of FIG. 7. As shown in FIG. 7, the lithography process includes a resist coating step S21, an exposing step S22, a developing step S23 and an annealing step S24.

In the resist coating step S21, the resist is applied onto the wafer, on which the circuit patter has been formed by using the CVD or the sputtering, and then in the exposing step S22, the applied resist is exposed. Then, in the developing step S23, the exposed resist is developed so as to obtain the resist pattern, and in the annealing step S24, the developed resist pattern is annealed to be made stable. Those steps S21 to S24 may be repeated by a desired number of layers.

According to the semiconductor device manufacturing method of the present invention, since the electron beam system as discussed with reference to FIG. 3 to FIG. 6 is used in the chip testing process S5 for testing the finished chips, therefore even in the case of the semiconductor device having a fine pattern, an image with a reduced distortion and/or out-of-focus can be obtained and thereby any defects in the wafer can be detected with high reliability.

Figure 11:
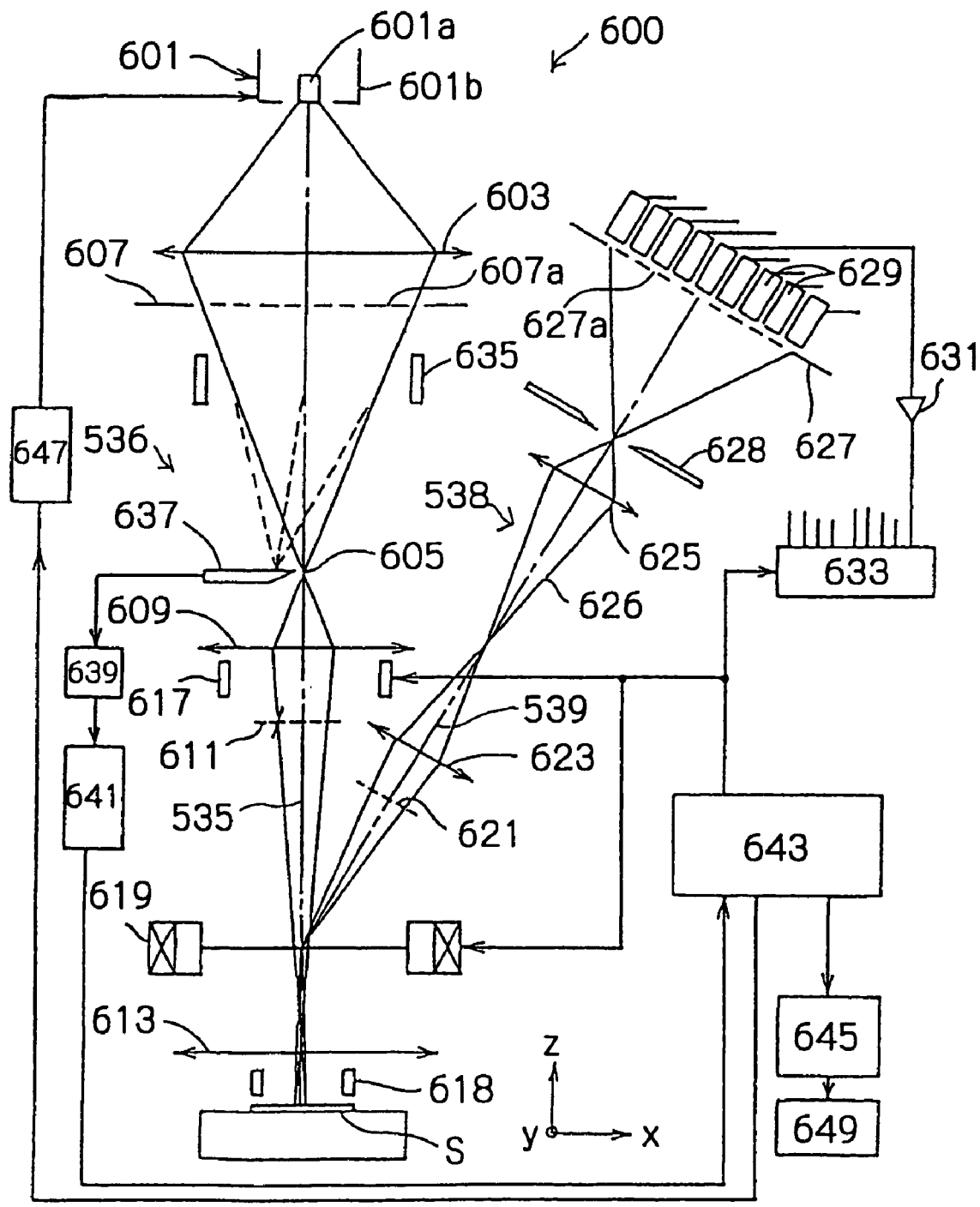
FIG. 11 is a general schematic diagram of an electron beam system (an electron optical system) according to an embodiment of the present invention.

FIG. 11 shows an electron beam system (an electron optical system) 600 to which the present invention can be applied. In FIG. 11, an electron beam emitted from a cathode 601a contained in an electron gun 601 is focused by a condenser lens 603 into a crossover image at a point 605. A first multi-aperture plate 607 having a plurality of apertures is disposed below the condenser lens 603, and with the aid of this, a plurality of primary electron beams is formed respectively. Each of the primary electron beams formed by the first multi-aperture plate 607 is demagnified by a demagnifying lens 609 so as to be projected onto a point 611. That beam is, after having been focused on the point 611, further focused by an objective lens 613 onto a sample S. The plurality of primary electron beams exiting from the first multi-aperture plate 607 is deflected so as to synchronously scan a surface of the sample S by a deflector 617 disposed between the demagnifying lens 609 and an objective lens 613.

In order to eliminate an image field curvature aberration of the demagnifying lens 609 and the objective lens 613, a plurality of small apertures are arranged along a circle on the multi-aperture plate 607 in such a manner that the projections of respective apertures in the Y-direction may be equally spaced. The electron gun 601, the condenser lens 603, the first multi-aperture plate 607, the deflector 617 and the objective lens 613 all together make up a primary optical system 536 having an optical axis 535.

A plurality of points on the sample S is irradiated by the thus focused plurality of primary electron beams respectively, and secondary electron beams emanated from said plurality of points are attracted by the electric field of the objective lens 613 to be converged narrower and then deflected by an E×B separator 619 to be introduced into a detecting system 538. Those secondary electron beams are focused at a point 621 closer to the objective lens 613 as compared with the point 611. This is because each of the primary electron beams has an energy of 500 eV on the sample surface, while in contrast, each of the secondary electron beams has only an energy of a few eV.

The detecting system 538 has magnifying lenses 623, 625, and the secondary electron beam after passing through those magnifying lenses 623, 625 passes through a plurality of apertures 627a of a second multi-aperture plate 627 and then is formed into images on a plurality of detectors 629. It is to be noted that each of the plurality of apertures 627a formed in the second multi-aperture plate 627 disposed in front of the plurality of detectors 629 corresponds respectively to each of a plurality of apertures 607a formed in the first multi-aperture plate 607 on the one-to-one basis.

Each of the detectors 629 converts the detected secondary electron beam into an electric signal indicative of its intensity. The electric signals output from respective detectors are amplified by the amplifier 631 and received by the image processing section 633, respectively, where the signals are converted into image data. Since the image processing section 633 is further provided with a scanning signal which has been used for deflecting the primary electron beam, the image processing section 633 can display an image representing the surface of the sample S. A defect in the surface of the sample S can be detected by comparing the image with a reference pattern, and also a line width of the pattern on the sample S can be measured by moving the sample S into the vicinity of the optical axis of the primary optical system 536 through the registration and then extracting a line width evaluation signal through a line scanning, which is then appropriately calibrated.

At this point, a special care must be taken in order to minimize an effect from three kinds of aberrations, i.e., the distortion induced in the primary optical system, the image field curvature aberration and the astigmatism when the primary electron beam after passing through the apertures of the first multi-aperture plate 607 is formed into an image on the surface of the sample S and the secondary electron beam emanated from the sample S is formed into an image on the detector 629.

Then, as to the relationship between a distance among a plurality of primary electron beams and the detecting system 538, if the primary electron beams are arranged to be spaced from each other by a distance greater than the aberration of the detecting system 538, cross talk among the plurality of electron beams can be eliminated. It is to be noted that in FIG. 11, reference numeral 626 illustrates trajectory of specific secondary electrons among those secondary electrons emanated from the irradiation points of the primary electron beam on a circle, which have been emanated from two points on a diameter of the circle in the directions normal to the sample surface. An aperture 628 is arranged in a location where those trajectories cross the optical axis 539, such that the aberration in the value converted into that on the sample surface may be made smaller than the minimum value of the beam-to-beam distance of the primary electron beams. Further, in FIG. 11, reference numeral 618 designates an axisymmetric electrode for measuring the potential of the pattern on the wafer.

As for the control of the dose, during fly-back of the scanning operation the multi-beam is deflected by a deflector 635 so as to be blocked by a knife edge 637 for blanking, while at the same time, the current absorbed into this knife edge is measured by an am meter 639, and the dose per unit area is calculated by a dose calculating circuit 641. The thus calculated value is stored in a storage 645 through a CPU 643.

Further, if the dose per unit area exceeds a predetermined value, the CPU 643 may invoke an electron gun control power supply 647 to decrease the voltage to be applied to a Wehnelt electrode 601b, thereby reducing the beam current to decrease the dose. Further, when the control is not able to catch up with the increase of the dose and ultimately the dose per unit area ends at a level higher than, for example, 3 μc/cm$^2$, then the data of the corresponding irradiation area is just output by an output means 649, and the evaluation is carried on.

Figure 12:
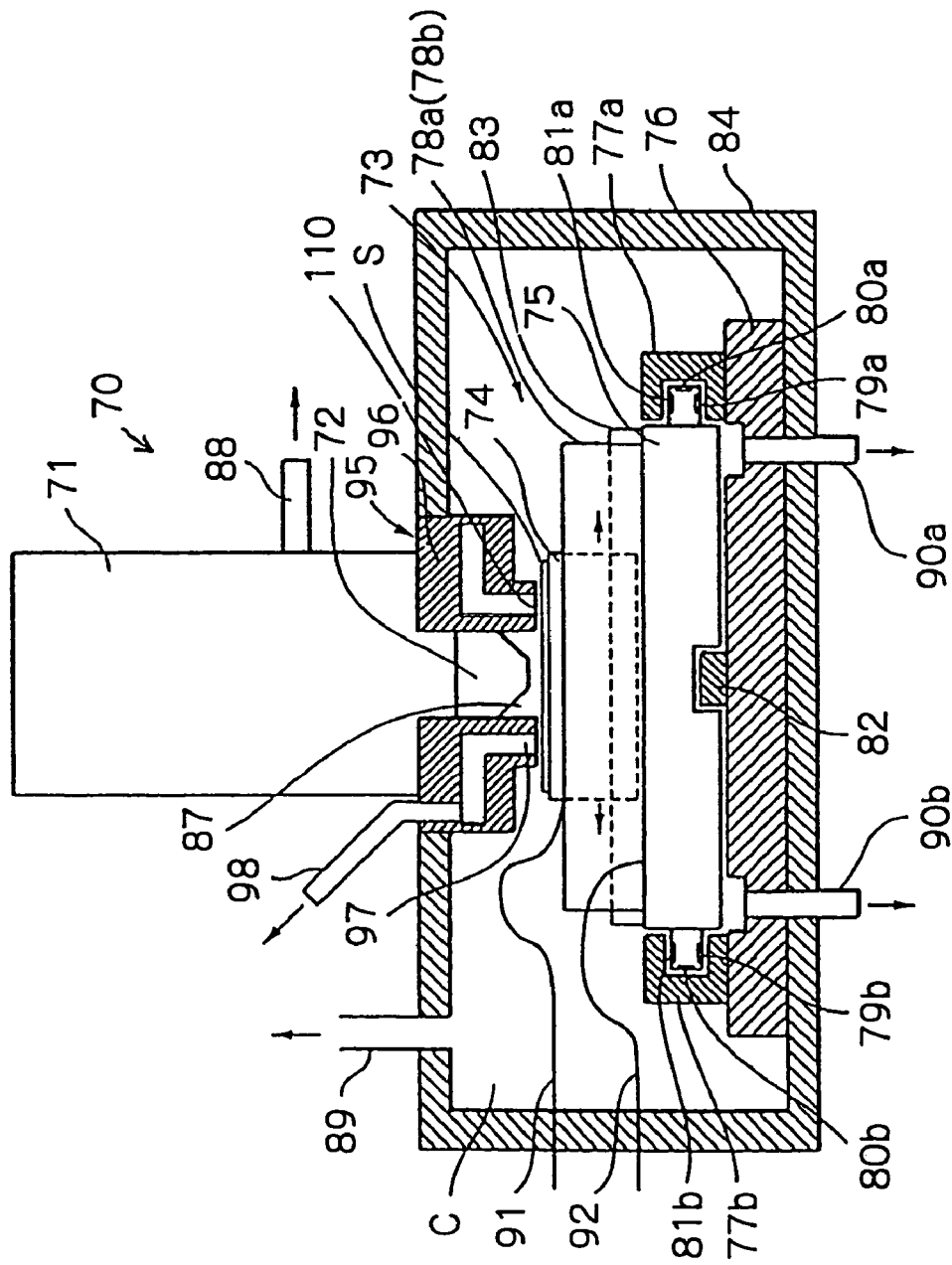
FIG. 12 is a general schematic diagram of an electron beam system (mainly, a movable table) according to an embodiment of the present invention.

FIG. 12 shows an electron beam system (mainly a movable stage) 70 to which the present invention can be applied. In this embodiment, a term "vacuum" means a vacuum typically referred to in this technical field. In the electron beam system 70 of FIG. 12, a tip end portion of a optical column 71 for irradiating an electron beam against a sample, i.e., an electron beam irradiation section 72, is installed in a housing 84 defining a vacuum chamber "C". Right below the optical column 71 is provided an XY stage 73 of high precision, in which an X table 74 movable in the X direction (the left and right direction in FIG. 12) is mounted on a Y-directionally (the direction vertical to the paper in FIG. 12) movable table 75. The sample S is loaded on the X table 74. The sample S is positioned correctly with respect to the optical column 71 by the XY stage 73, so that an electron beam from the optical column 71 may be irradiated onto a predetermined point on a surface of the sample.

A pedestal 76 of the XY stage 73 is fixed to a bottom wall of the housing 84, and the Y table 75 movable in the Y direction (the vertical direction with respect to the paper in FIG. 12) is mounted on the pedestal 76. On both side faces of the Y table 75 (a left and a right side faces in FIG. 12), protrusions are formed, which are protruded into concave recesses formed in a pair of Y-directional guides 77a and 77b in their side surfaces facing to the Y table respectively. Each of the concave recesses extends in the Y direction along almost the full length of each of the Y-directional guides.

Hydrostatic bearings 81a, 79a, 81b, 79b having a known structure are provided respectively in an upper and a lower faces and side faces of the protrusions protruding into the concave recesses, and a high pressure gas is blown out via those hydrostatic bearings, so that the Y table 75 can be supported in a non-contact manner with respect to the Y-directional guides 77a, 77b and thereby allowed to make a reciprocating motion in the Y direction smoothly. Further, a linear motor 82 having a known structure is disposed between the pedestal 76 and the Y table 75 and a Y directional driving is performed by the linear motor 82. A high pressure gas is supplied to the Y table 75 through a flexible pipe 92 for feeding the high pressure gas, and further distributed to the hydrostatic bearings 79a to 81a and 79b to 81b through a gas passage (not shown) formed within the Y table. The high pressure gas supplied to the hydrostatic bearings is blown out into a gap in a range of some microns to some ten microns formed between the Y table and a oppositely positioned guide plane of each of the Y directional guides, and herein the high pressure gas has a role in positioning the Y table 75 accurately with respect to the guide planes in the X direction and the Z direction (in the up and down direction in FIG. 12).

The X table 74 is operatively mounted on the Y table 75 so as to be movable in the X direction (the left and right direction in FIG. 12). A pair of X directional guides 78a, 78b (only 78a is shown) having the same structure as that of the Y directional guides 77a, 77b is disposed on the Y table 75 with the X table 74 interposed therebetween. A concave recess is also formed in each of the X directional guides in their side surfaces facing to the X table 74. Each of the concave recesses extends along almost full length of each of the X directional guides. Hydrostatic bearings (not shown) similar to said hydrostatic bearings 81a, 79a, 80a, 81b, 79b, 80b are arranged in a similar orientation in upper and a lower faces and side faces of each protrusion of the X directional table 74 protruding into the concave recess. A linear motor 83 having a known structure is disposed between the Y table 75 and the X table 74, and the X directional driving of the X table is performed by that linear motor 83.

A high pressure gas is supplied to the X table 74 through a flexible pipe 91 and further distributed to the hydrostatic bearings. This high pressure gas is blown out against the guide plane of the X directional guide from the hydrostatic bearings, and thereby the X table 74 can be supported with high precision with respect to the Y directional guide in the non-contact manner. A vacuum chamber "C" is evacuated by a vacuum pump or the like having a known structure through vacuum pipes 89, 90a, 90b connected thereto. Inlet sides of the pipes 90a, 90b (inside of the vacuum chamber) are extended through the pedestal 76 and open in the upper surface thereof in the vicinity of a location where the high pressure gas is discharged from the XY stage 73, so that the increase in the pressure in the vacuum chamber may be prevented as much as possible, which may otherwise be caused by the high pressure gas blown out from the hydrostatic bearings.

A differential exhaust mechanism 95 is arranged in the surrounding of the electron beam irradiation section 72 or the tip end of the optical column 71 so as to keep the pressure within the electron beam irradiation space 87 to be sufficiently low even if the pressure within the vacuum chamber C is high. That is, an annular member 96 of the differential exhaust mechanism 95 mounted to the periphery of the electron beam irradiation section 72 is positioned with respect to the housing 94 such that a minute gap 110 (in a range of some microns to some ten microns) may be created between the lower surface of the annular member 96 (the surface facing to the sample S) and the sample S, and an annular groove 97 is formed in the under surface of the annular member 96.

The annular groove 97 is connected to a vacuum pump, though not shown, via an exhaust pipe 98. Accordingly, the minute gap 110 may be evacuated through the annular groove 97 and the exhaust port 98, so that any gas molecules trying to enter the electron beam irradiation space 87 surrounded by the annular member 96 from the vacuum chamber C can be exhausted. By way of this, the pressure within the electron beam irradiation space 87 can be kept to be low, and thereby the electron beam can be irradiated without causing any problem. This annular groove may employ a double or a triple structure depending on the pressure within the chamber and/or the pressure within the electron beam irradiation space 87.

As the high pressure gas to be supplied to the hydrostatic bearings, typically dry nitrogen gas may be employed. However, if possible, preferably an inert gas of higher purity should be used. This is because if any impurities, such as water content or oil content, are contained in the gas, those impurities may adhere to the inner surface of the housing defining the vacuum chamber or to the surfaces of the stage components, which in turn deteriorate the vacuum level, or otherwise they may adhere to the surface of the sample, which also in turn reversely affect the vacuum level in the electron beam irradiation space. Typically, the sample S is not directly loaded on the X table, but may be loaded on a sample table having functions for detachably holding the sample and/or for applying a minor position change with respect to the XY stage 73.

Since the stage mechanism of the hydrostatic bearing used in the atmosphere may be employed in the electron beam system 70 almost without any modification, an XY stage having as high precision as the stage specified for the atmosphere used in the exposing apparatus can be achieved for the XY stage specified for the electron beam system with approximately the same cost and size. The structure and configuration for the hydrostatic guide and the actuator (linear motor) as described above have been given by way of example only, but any hydrostatic guide and actuator usable in the atmosphere can be employed.

Figure 9:
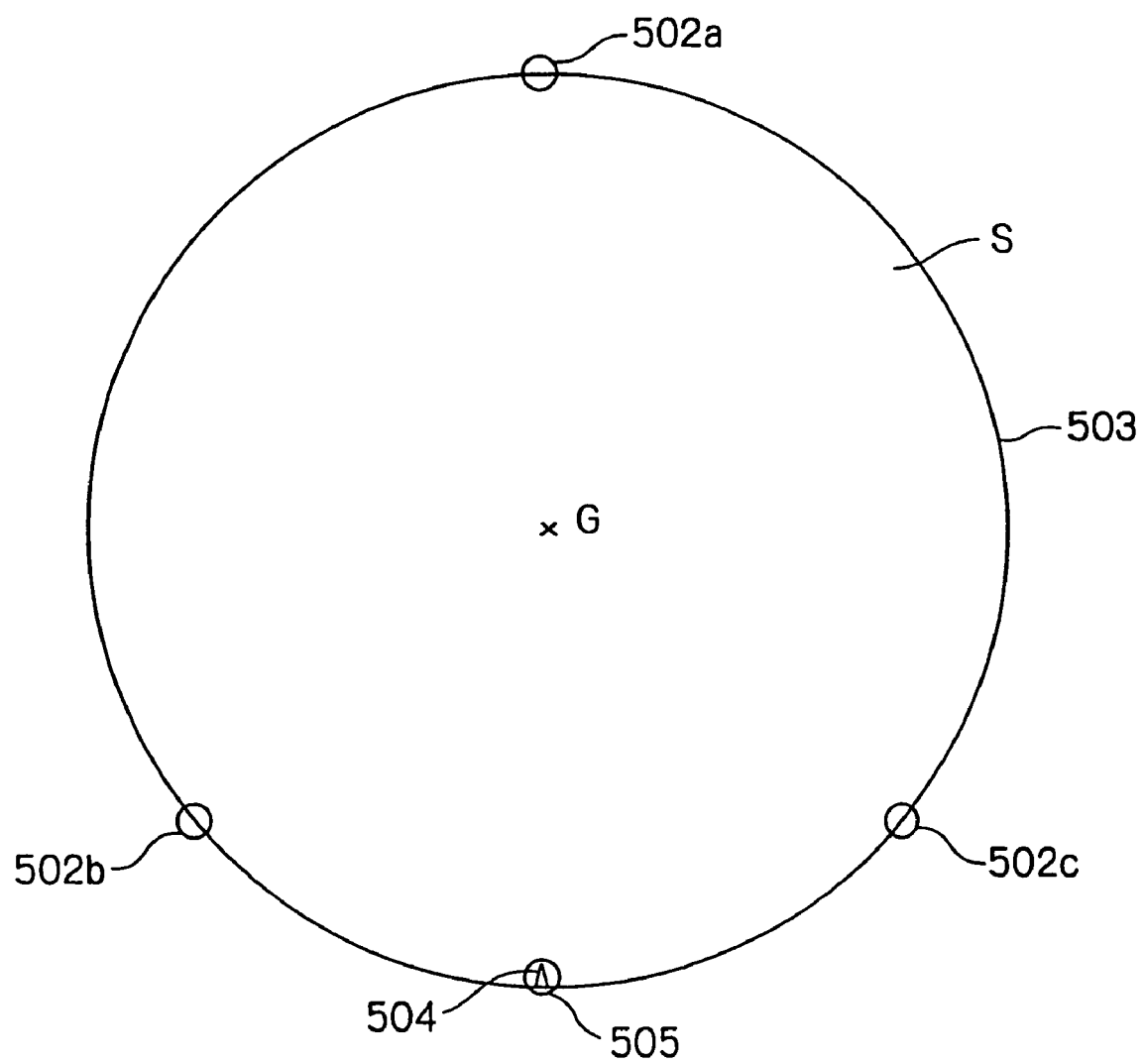
FIG. 9 is general schematic diagram showing an arrangement of an electrostatic capacity sensor in an electron beam system according to an embodiment of the present invention.

FIG. 9 is a general schematic diagram illustrating an arrangement of an electrostatic capacity sensor in an electron beam system according to an embodiment of the present invention. In the electron beam system, four electrostatic capacity sensors 502a, 502b, 502c and 505 are disposed along a periphery 503 of a disc shaped 12 inch wafer 1 to be loaded on the movable stage, which is not shown. Three of the sensors 502a, 502b and 502c are arranged so as to be equally spaced from each other, while the sensor 505 is provided to adjust a rotational orientation of the wafer and is disposed in a location between the sensor 502b and the sensor 502c where a notch 504 or an orientation flat should be normally located. Herein, the notch or the orientation flat is provided by cutting out a portion of the contour of the disc-like wafer in order to specify the direction of rotation of the wafer. The notch is defined as a V-shaped cut-out, while the orientation flat is a linear cut-out normal to a radial direction of the wafer. A position of each of the electrostatic capacity sensors 502a, 502b, 502c and 505 with respect to the wafer on the movable stage may be determined such that the wafer may overlap approximately a half of each electrode. A distance (dx, dy) between an optical axis (0, 0) of the electron optical system and the center of gravity of three electrostatic capacity sensors 502a, 502b and 502c is measured in advance.

Positioning of the wafer loaded on the electron beam system may be carried out in the following manner. The disc-like wafer S mounted on the movable stage is brought by the movement of the movable stage into a position where the periphery 503 of the wafer comes into engagement with respective electrostatic capacity sensors 502a, 502b, 502c and 505, as shown in FIG. 9. At first, the electrostatic capacity is measured by three of the sensors 502a, 502b and 502c which have been disposed to be spaced equally from each other, and the measured values from those three sensors 502a, 502b and 502c are compared to one another, and then the xy position of the wafer is adjusted by the movable stage such that those three sensors may indicate the same measured values.

In the case where the wafer is in a location offset to the right hand side in FIG. 9, since the measured value from the sensor 502c may be greater, while the measured value from the sensor 502b may be smaller, therefore the wafer is shifted to the left hand side so as to make both measured values equal. If the measured value from the sensor 502a is smaller than the measured value from the sensor 502b, the wafer should be shifted upwardly, and if greater, then the wafer should be shifted downwardly to make the measured values equal to each other. In this way, the center position (the center of gravity position G) of the wafer can be made to match the center of gravity position for the three sensors 502a, 502b and 502c, or the optical axis position (0, 0) of the electron optical system. After this, in order to correct the rotational orientation of the wafer, a θ table is moved to minimize the measured value from the electrostatic capacity sensor 505.

In the above embodiment, the four electrostatic capacity sensors 502a, 502b, 502c and 505 are used to position the wafer relative to the movable stage with a position accuracy of ±20 μm and a rotation accuracy of ±10 mrad. By moving the movable stage by the distance (dx, dy), the center of the wafer can be brought into a position right below the electron optical system or the optical axis position (0, 0) thereof so as to match therewith with the position accuracy of ±20 μm.

When the field of view of the electron optical system is defined by a diameter of 200 μm, a corner portion (an edge) created by 100 μm wide dicing lines can be obtained in an SEM image. The dicing line is defined as a region containing no device pattern arranged between dies and it has a width slightly greater than the thickness of a saw blade used for cutting out dies from the wafer so as to separate one die from another die in the X direction and the Y direction. It can be accurately measured from the SEM image how much the center position of the wafer is offset from that of the electron optical system. Therefore, upon performing defect inspection of the pattern, this offset is compensated for on the basis of the SEM image and then the comparison is made relative to the reference pattern, thereby making it possible to detect the defect.

Discussing now a problem that the rotational orientation of the wafer may fall only within a range of ±10 mrad, any offset of the rotational orientation can be accurately measured by moving the movable stage into a position where the optical axis of the electron optical system comes into match with the dicing line in the periphery of the wafer, taking the SEM image in that position and then comparing it to that taken in the center to determine the offset therebetween. The correction may be performed with the θ table, or alternatively the stage may be run along the orientation of the pattern on the wafer during the continuous driving of the stage.

A method for evaluating an image, in which alignment has not been accomplished correctly, by using a pattern matching will be described with reference to FIG. 10. FIG. 10a is an SEM image including a field of view 521 obtained by the electron optical system, while FIG. 10b is a reference image including a field of view 522. By comparing respective pattern corner portions 525, 526, 527, 528 in the vicinity of four corners of the field of view 521 of the SEM image with respective pattern corner portions 525', 526', 527', 528' in the vicinity of four corners of the reference image including the field of view 522 to one another, respectively, those offsets in position, rotation and magnification of the SEM image from the reference image can be calculated.

The reason why four points are selected in each image is to allow a pattern matching to be conducted correctly, even if the defects reside in the pattern corner portions to be compared. As shown in FIG. 10a, if a defect 529 happens to reside in the vicinity of the pattern corner portion 252, a magnification compared in 525-527, or (a distance between 525 and 527)/(a distance between 525' and 527'), may be different from a magnification compared in 526-528, or (a distance between 526-528)/(a distance between 526' and 528'), which indicates that there must be a defect in some pattern. In this case, if further a magnification measured in 525-528 is compared to a magnification measured in 526-527, the result would be, for example, (525-527)/(525'-527')=1.01
(526-528)/(526'-528')=1.05
(526-527)/(526'-527')=1.05
(525-528)/(525'-528')=0.99 which indicates that the pattern corner 525 must contain the defect. It is a matter of course that the rotation angle may be compared.

FIG. 10c shows a case of a pattern corner shaped into arc 531. In this case, an accurate evaluation of a pattern can be obtained by considering an intersection 526 of extensions of two sides to be a pattern corner.

An electron beam system according to the present invention shown in FIG. 11 may be applicable to a semiconductor device manufacturing method shown in FIG. 7 and FIG. 8. That is, the electron beam system of FIG. 11 is applicable to the process for evaluating a processed condition of a wafer (wafer testing) in the wafer processing process, and if applied to the chip testing process for inspecting the finished chip, then a defect in a wafer can be detected with high accuracy.

FIG. 13a and FIG. 13b are diagrams for illustrating a position sensor 540 of electrostatic capacity type, wherein FIG. 13a is a plan view showing a physical relationship between an electrode of the position sensor and a wafer, while FIG. 13b contains a side elevational view showing a physical relationship between the electrode of the position sensor and the wafer as well as a block diagram of other main components. As shown in FIG. 13a and FIG. 13b, an electrode 541 of the position sensor 540 has an elongated plate-like shape and it is positioned in parallel with the surface of the wafer S as spaced from the surface by a predetermined distance "H". The wafer S and the electrode 541 are electrically connected to an electrostatic capacity measuring instrument 546, and an electrostatic capacity "Q" between these two components is measured. The electrostatic capacity measuring instrument 546 may be a commercially available impedance measuring instrument.

The electrostatic capacity Q between the wafer S and the electrode 541 is proportional to an overlapped area 542 of the wafer S with respect to the electrode 541. As shown in FIG. 13a, assuming that the shape of the electrode 541 is a rectangle and the electrode 541 is disposed in the radial direction of the wafer, then the area of the overlapped portion 542 may be proportional to a length "x" of the overlapped portion of the electrode 541 with respect to the wafer S in the radial direction thereof. Accordingly, by preparing a comparison table 547 containing a relationship between the length "x" and the electrostatic capacity Q, which has been determined in advance, the overlapped portion length "x", or the position of the wafer S, can be determined on the basis of the comparison table and the measured electrostatic capacity Q. As shown in FIG. 13b, the measured electrostatic capacity Q and the data from the comparison table 547 are input into the position detector 548, which in turn outputs the wafer position data.

EFFECTS OF THE INVENTION

According to the present invention, the following effects may be brought about.

(1) As compared with an optical system using a three-stage of lenses according to the prior art, in the present invention, a number of stages of lenses can be reduced to two, and accordingly a lens axis aligning device may be made one stage less. Consequently, a length of an optical path may be made shorter and out-of-focus of an electron beam due to a space charge effect may be reduced. Further in the present invention, since a number of parts to be used in the optical system and a control circuit can be reduced by a number corresponding to one-stage of lens and one-stage of electrostatic deflector, therefore a reliability of the electron beam system can be improved.

(2) As compared to a crossover image demagnification type beam, in the present invention, a higher beam current can be obtained by using the same electron beam size.

(3) Since the electron gun can be operated in the space charge limited condition, a shot noise in the electron beam can be significantly reduced, and thereby a noise in the secondary electrons signal can be reduced.

(4) Since a NA aperture is disposed in a front location with respect to a demagnification lens, a detector of the secondary electrons can be disposed in a front location with respect to an objective lens.

(5) When the NA aperture is disposed adjacent to the objective lens, it is no more necessary to accurately position a crossover image point of the electron beam.

(6) Since the electron gun is used in the space charge limited condition, a signal having a greater S/N ratio can be obtained by using the same level of beam current as compared to the case of using an electron gun of the schottky cathode type. In this case, preferably a shot noise reduction coefficient is 0.5 or lower, and more preferably 0.2 or lower.

(7) Since the secondary electrons generated from a pattern of high voltage can be returned back toward the sample by applying a voltage lower than that of the sample to an electrode most proximal to the sample among the electrodes of the objective lens, therefore not only the potential contrast can be measured but also upon obtaining an SEM image, the secondary electrons can be detected with high efficiency by grounding this electrode.

(8) Upon measuring the potential of the sample, an inspection can be finished within a shorter time as compared to a full surface scanning by applying an irradiation selectively only to a location containing a via.

(9) Since an optimal operating condition, for example, a beam diameter, can be set selectively in each individual case for obtaining the SEM image, for giving charges to the sample, or for measuring a potential contrast, therefore an inspection with high precision can be achieved with high throughput.

(10) Since a defect inspection can be carried out with high throughput, therefore a device can be manufactured with high yield.

(11) An inspection apparatus of the present invention can provide an innovative electron beam system, in which an inspection of a wafer can be performed without destroying a gate oxide or the like by performing an alignment operation without using any electron beam.

(12) According to the present invention, since an optical microscope for alignment operation is not required to be installed in a vacuum environment, an electron beam system may have a more simplified structure and thereby can be manufactured at lower price. Further, there would be no more alignment time, and so a throughput (a processing volume per time) can be improved.

(13) According to the present invention, a pattern matching is conducted by using four or more points, so that no error may be produced even if a defect resides at a point to be evaluated, and also a pattern matching can be performed correctly even if a corner portion of the pattern has a curvature.

What is claimed is:

1. An electron beam system comprising:
   a primary optical system for irradiating a plurality of electron beams onto a sample;
   a condenser lens for focusing the plurality of electron beams into a crossover image at a point;
   a first deflector disposed downstream to the point for scanning the plurality of electron beams; and
   a second deflector disposed upstream to the point for scanning the plurality of electron beams;
   a dose amount calculating circuit; a CPU for controlling a voltage applied to a Wehnelt electrode; and
   wherein the plurality of electron beams are simultaneously blocked by a knife edge disposed at the point from passing toward the sample for measuring electric current absorbed by the knife edge when a signal is applied to the second deflector and during a fly-back, and the dose amount calculating circuit calculates a dose amount per unit area from the electric current absorbed by the knife edge, and the CPU decreases the voltage applied to the Wehnelt electrode for reducing a beam current when the dose amount exceeds a predetermined value.

2. An electron beam system according to claim 1, further comprising an output means for outputting an irradiation area irradiated by the plurality of electron beams of which dose amount is higher than 3 μc/cm$^2$.

3. An electron beam system according to claim 2, further comprising an ampere meter for measuring electric current absorbed by the aperture when the plurality of electron beams are blocked from passing toward the sample.

4. An electron beam system according to claim 2, further comprising an objective lens made of an electrostatic lens having three pieces of electrodes, and a power supply for applying a negative voltage to the sample, wherein a second electrode counted from the sample is applied with a positive high voltage, and a voltage applied to an electrode disposed at the electron gun side of the second electrode is varied so that field curvature aberration is corrected.

5. An electron beam system comprising:
   a plurality of apertures for forming a plurality of primary electron beams;
   a primary optical system for irradiating a plurality of electron beams on to a sample;
   an electron gun of which Wehnelt electrode voltage is adjusted so that a crossover image forms at a NA aperture;
   a condenser lens for focusing the plurality of electron beams into a second crossover image at a principal plane of an objective lens;
   a first deflector for scanning the plurality of electron beams;
   a second deflector for deflecting the plurality of electron beams and blocking the plurality of electron beams by a knife edge which is disposed at the point for measuring electric current absorbed by the knife edge when a signal is applied to the second deflector and during a fly-back,
   and calculating a dose amount per unit area from the electric current absorbed by the knife edge
   the objective lens for focusing the primary electron beams passed through the apertures on a sample, and
   a secondary optical system having a beam separator with an electromagnetic deflector for separating secondary electron beams emanated from the sample from the primary electron beams, and at least a lens for magnifying the secondary electron beams separated by the beam separator to form into an image on a detector.

6. An electron beam system according to claim 5, further comprising in a sample side of the plurality of apertures, a deflector and a member for preventing passing the plurality of primary electron beams toward the sample, wherein a signal applied to the deflector prevents simultaneously passing the plurality of primary electron beams toward the sample.

7. An electron beam system according to claim 5, further comprising axisymmetric electrodes below the objective lens, the axisymmetric electrodes being applied with a voltage which is lower than that applied to the sample so that the secondary electrons emanated from the sample are selectively passed to the detector.

8. An electron beam system according to claim 5, further comprising a single electron gun so that the plurality of apertures are irradiated by an electron beam emitted from the single electron gun.

9. An electron beam system according to claim 8, wherein the single electron gun is operated within a space charge limited zone.

* * * * *